(12) United States Patent
Marnfeldt et al.

(10) Patent No.: US 9,707,395 B2
(45) Date of Patent: Jul. 18, 2017

(54) CIRCUITRY FOR CHARGING A BATTERY IN AN IMPLANTABLE MEDICAL DEVICE IN ACCORDANCE WITH HISTORICAL PARAMETERS IMPACTING BATTERY CAPACITY

(71) Applicant: Boston Scientific Neuromodulation Corporation, Valencia, CA (US)

(72) Inventors: Goran N. Marnfeldt, Valencia, CA (US); Rafael Carbunaru, Valley Village, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/593,708

(22) Filed: Jan. 9, 2015

(65) Prior Publication Data
US 2015/0196764 A1 Jul. 16, 2015

Related U.S. Application Data

(60) Provisional application No. 61/928,352, filed on Jan. 16, 2014.

(51) Int. Cl.
*A61N 1/378* (2006.01)
*A61N 1/36* (2006.01)
(Continued)

(52) U.S. Cl.
CPC ......... *A61N 1/36128* (2013.01); *A61N 1/378* (2013.01); *A61N 1/3787* (2013.01);
(Continued)

(58) Field of Classification Search
CPC ......... A61N 1/378; A61N 1/3787; A61N 1/08
See application file for complete search history.

(56) References Cited

U.S. PATENT DOCUMENTS 6,020,778 A 2/2000 Shigehara et al.
6,516,227 B1 2/2003 Meadows et al.
(Continued)

FOREIGN PATENT DOCUMENTS

CN 101312259 A 11/2008
JP 2008-252960 A 10/2008
(Continued)

OTHER PUBLICATIONS

U.S. Appl. No. 61/877,871, filed Sep. 13, 2013, Funderburk.
(Continued)

*Primary Examiner* — Michael Kahelin
(74) *Attorney, Agent, or Firm* — Lewis, Reese & Nesmith, PLLC

(57) ABSTRACT

An algorithm programmed into the control circuitry of a rechargeable-battery Implantable Medical Device (IMD) is disclosed that can adjust the charging current (Ibat) provided to the rechargeable battery over time (e.g., the life of the IMD) in accordance with one or more of the parameters having an effect on rechargeable battery capacity, such as number of charging cycles, charging current, discharge depth, load current, and battery calendar age. The algorithm consults such parameters as stored over the history of the operation of the IMD in a parameter log, and in conjunction with a battery capacity database reflective of the effect of these parameters on battery capacity, estimates a change in the capacity of the battery, and adjust the charging current in one or both of trickle and active charging paths to slow the loss of battery capacity and extend the life of the IMD.

14 Claims, 14 Drawing Sheets

(51) Int. Cl.
    *H02J 7/00*     (2006.01)
    *A61N 1/37*     (2006.01)

(52) U.S. Cl.
    CPC ........ *A61N 1/3605* (2013.01); *A61N 1/36125* (2013.01); *A61N 1/3708* (2013.01); *A61N 2001/36039* (2013.01); *H02J 7/0057* (2013.01)

(56) References Cited

U.S. PATENT DOCUMENTS

| | | |
|---|---|---|
| 7,177,698 B2 | 2/2007 | Klosterman et al. |
| 7,962,222 B2 | 6/2011 | He et al. |
| 8,649,858 B2 | 2/2014 | Griffith et al. |
| 8,666,504 B2 | 3/2014 | Dronov et al. |
| 8,744,592 B2 | 6/2014 | Carbunaru et al. |
| 8,781,596 B2 | 7/2014 | Aghassian et al. |
| 2007/0038250 A1* | 2/2007 | He .................... A61N 1/36185 607/2 |
| 2012/0095529 A1 | 4/2012 | Parramon et al. |
| 2013/0023943 A1 | 1/2013 | Parramon et al. |
| 2013/0096651 A1 | 4/2013 | Ozawa et al. |
| 2013/0193912 A1* | 8/2013 | Bornhoft ............... H02J 7/0083 320/108 |
| 2013/0193914 A1 | 8/2013 | Gaddam et al. |
| 2014/0249603 A1 | 9/2014 | Yan et al. |

FOREIGN PATENT DOCUMENTS

| | | |
|---|---|---|
| WO | 00/59095 A1 | 10/2000 |
| WO | 2013/012487 A1 | 1/2013 |

OTHER PUBLICATIONS

U.S. Appl. No. 61/873,314, filed Sep. 3, 2013, Tahmasian.
U.S. Appl. No. 61/891,730, filed Oct. 16, 2013, Lamont et al.
International Search Report and Written Opinion regarding corresponding PCT Application No. PCT/US2015/011005, dated May 7, 2015.
Office Action regarding corresponding Japanese Patent Application No. 2016-565097, mailed May 29, 2017.

* cited by examiner

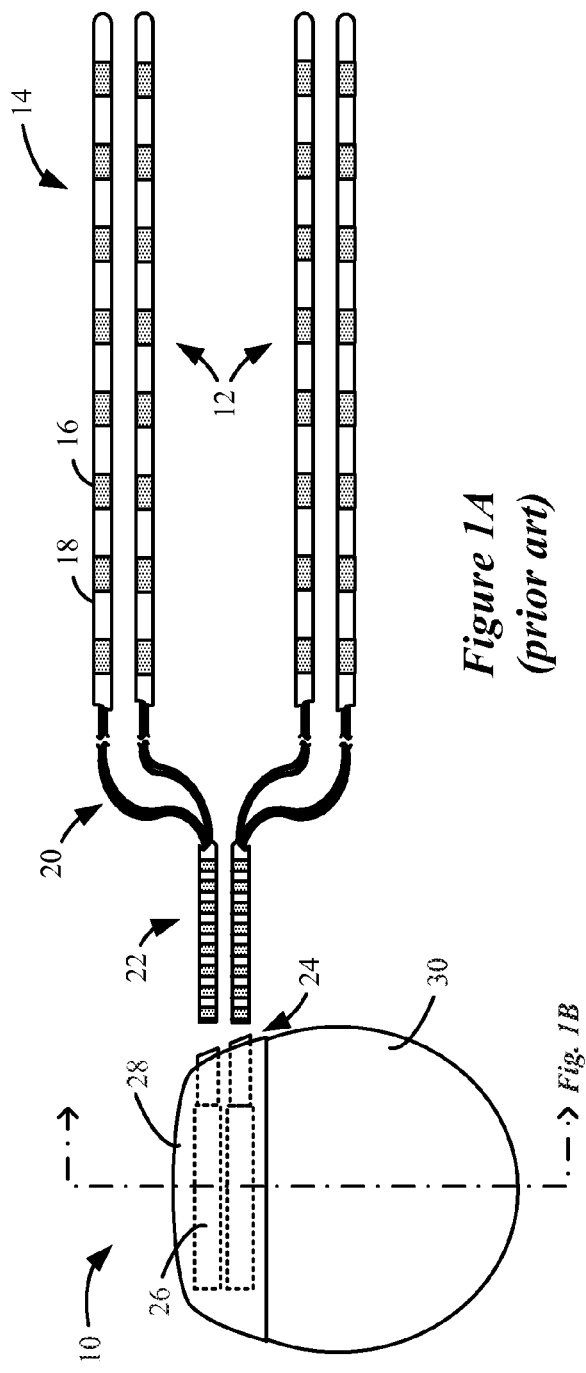
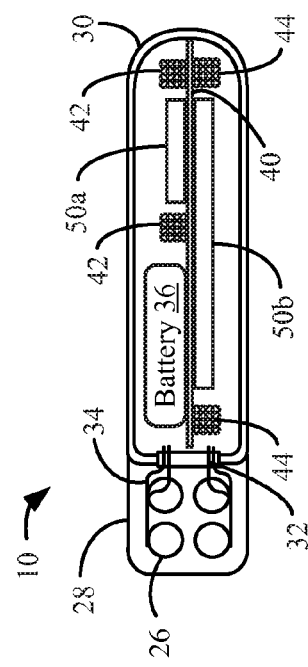
*Figure 1A (prior art)*
*Figure 1B (prior art)*

| Charging session (Nc) | Timestamp | Charging time (Tc) (min) | Vbat(i) | Vbat(f) | ΔVbat= Vbat(f)- Vbat(i) | Ibat (mA) | Charge (Cc) = Ibat*Tc |
|---|---|---|---|---|---|---|---|
| 1 | t1 | 13.2 | 2.5 | 4.15 | 1.65 | 40 | 528 |
| 2 | t3 | 6.6 | 3.3 | 4.1 | 0.8 | 40 | 264 |
| 3 | t5 | 13.0 | 3.45 | 4.15 | 1.7 | 40 | 520 |
| 4 | t7 | 14.1 | 2.2 | 4.2 | 2.0 | 37 | 518 |
| 5 | t9 | 8.7 | 3.0 | 4.1 | 1.1 | 40 | 348 |
| 6 | t11 | 12.6 | 2.5 | 4.15 | 1.65 | 40 | 504 |
| ⋮ | | | | | | | |
| 104 | t207 | 13.4 | 4.1 | 1.5 | 2.6 | 36 | 482 |
| 105 | t209 | 14.0 | 4.0 | 1.8 | 2.2 | 34 | 476 |
| 106 | t211 | 12.9 | 4.05 | 1.75 | 2.3 | 36 | 464 |

⟩ 120c

| Use Session (Nu) | Timestamp | Use time (Tu) (min) | Iload (mA) | Charge (Cu) = Iload*Tu |
|---|---|---|---|---|
| 1 | t0 | Tu1 | Iload1 | Cu1 |
| 2 | t2 | Tu2 | Iload2 | Cu2 |
| 3 | t4 | Tu3 | Iload3 | Cu3 |
| 4 | t6 | Tu4 | Iload4 | Cu4 |
| 5 | t8 | Tu5 | Iload5 | Cu5 |
| 6 | t10 | Tu6 | Iload6 | Cu6 |
| ⋮ | | | | |
| 104 | t206 | 13.4 | Iload 104 | Cu104 |
| 105 | t208 | 14.0 | Iload105 | Cu105 |
| 106 | t210 | 12.9 | Iload106 | Cu106 |

⟩ 120u

| Calendar age (A) |
|---|
| tcurrent |

⟩ 120a

Capacity-relevant parameter log 120

*Figure 5A*

Present capacity-relevant parameters 120'

| Cc(tot) | Nc | ΔVbat(avg) | Ibat(avg) | Cu(tot) | Iload(avg) | Calendar age (A) | Charge ratio (Z) = Cu(tot)/Cc(tot) |
|---|---|---|---|---|---|---|---|
| Cc(tot)2 | Nc4 | ΔVbat(avg)3 | Ibat(avg)6 | Cu(tot)2 | Iload(avg)4 | A3 | Z2 |

*Figure 5B*

Battery capacity database 122

| Cc(tot) | Nc | ΔVbat(avg) | Ibat(avg) | Cu(tot) | Iload(avg) | Calendar age (A) | Charge ratio (Z) | % change in battery capacity |
|---|---|---|---|---|---|---|---|---|
| Cc(tot)1 | Nc1 | ΔVbat(avg)1 | Ibat(avg)1 | Cu(tot)1 | Iload(avg)1 | t1 | Z3 | -1% |
| Cc(tot)2 | Nc2 | ΔVbat(avg)2 | Ibat(avg)2 | Cu(tot)2 | Iload(avg)2 | t2 | Z2 | -2% |
| Cc(tot)3 | Nc3 | ΔVbat(avg)3 | Ibat(avg)3 | Cu(tot)3 | Iload(avg)3 | t3 | Z1 | -3% |

| | Cc(tot) | Nc | ΔVbat(avg) | Ibat(avg) | Cu(tot) | Iload(avg) | Calendar age (A) | Charge ratio (Z) |
|---|---|---|---|---|---|---|---|---|
| Weight | 1 | 0.3 | 0.5 | 0.1 | 0.6 | 0.15 | 0.2 | 0.8 |
| Priority | 1 | 5 | 4 | 8 | 3 | 7 | 6 | 2 |

*Figure 5C*

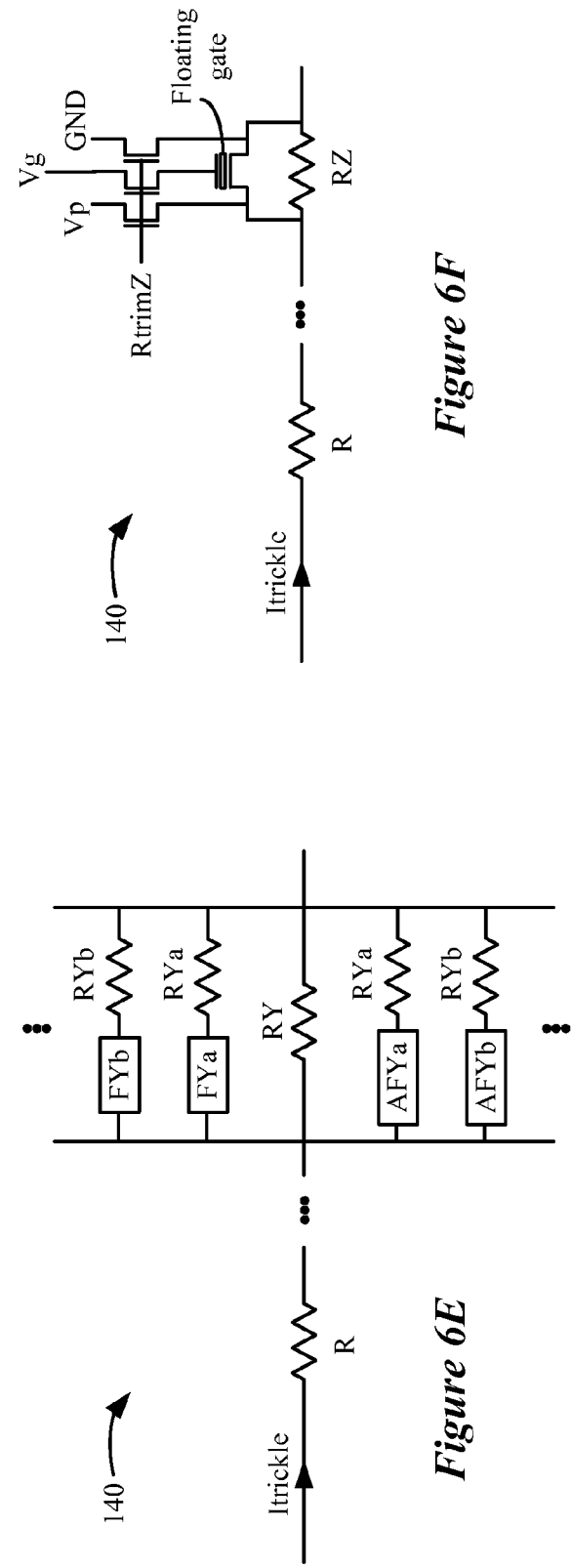
*Figure 6D*
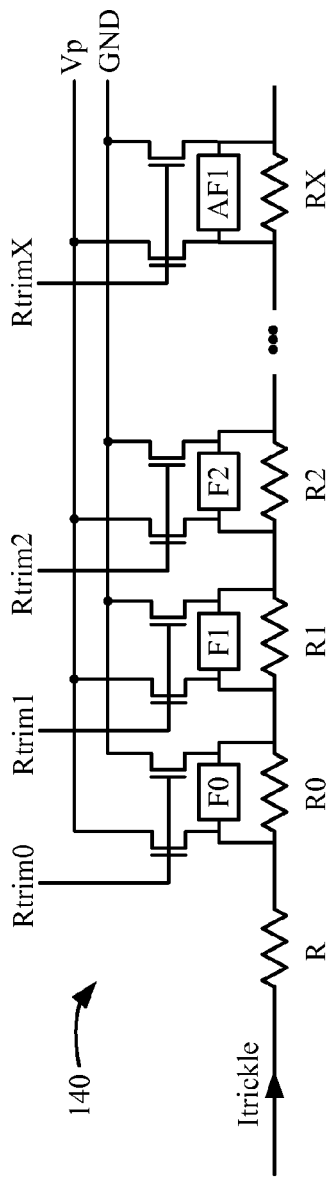
*Figure 6E*
*Figure 6F*

CIRCUITRY FOR CHARGING A BATTERY IN AN IMPLANTABLE MEDICAL DEVICE IN ACCORDANCE WITH HISTORICAL PARAMETERS IMPACTING BATTERY CAPACITY

CROSS REFERENCE TO RELATED APPLICATIONS

This is a non-provisional of U.S. provisional patent application Ser. No. 61/928,352, filed Jan. 16, 2014, to which priority is claimed, and which is incorporated herein by reference in its entirety.

This application is related to U.S. provisional patent applications 61/928,342 and 61/928,391, both filed Jan. 16, 2014, which are both incorporated herein by reference in their entireties.

FIELD OF THE INVENTION

This application relates to the field of implantable medical devices, and in particular to battery charging circuitry for an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

An SCS system typically includes an Implantable Pulse Generator (IPG) 10 shown in plan and cross-sectional views in FIGS. 1A and 1B. The IPG 10 includes a biocompatible device case 30 that holds the circuitry and battery 36 necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 28 on the IPG 10, which header can comprise an epoxy for example. Once inserted, the proximal contacts 22 connect to header contacts 26, which are in turn coupled by feedthrough pins 34 through a case feedthrough 32 to circuitry within the case 30.

In the illustrated IPG 10, there are thirty-two lead electrodes (E1-E32) split between four leads 14, with the header 28 containing a 2×2 array of lead connectors 24. However, the number of leads and electrodes in an IPG is application specific and therefore can vary. In a SCS application, the electrode leads 14 are typically implanted proximate to the dura in a patient's spinal cord, and when a four-lead IPG 10 is used, these leads are usually split with two on each of the right and left sides of the dura. The proximal electrodes 22 are tunneled through the patient's tissue to a distant location such as the buttocks where the IPG case 30 is implanted, at which point they are coupled to the lead connectors 24. A four-lead IPG 10 can also be used for Deep Brain Stimulation (DBS) in another example. In other IPG examples designed for implantation directly at a site requiring stimulation, the IPG can be lead-less, having electrodes 16 instead appearing on the body of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 50a and 50b coupled to top and bottom surfaces of the PCB; a telemetry coil 42 for wirelessly communicating with an external controller (not shown); a charging coil 44 for wirelessly receiving a magnetic charging field from an external charger 90 (FIG. 2) for recharging the battery 36; and the feedthrough pins 34 (connection not shown). If battery 36 is permanent and not rechargeable, charging coil 44 would be unnecessary. (Further details concerning operation of the coils 42 and 44 and the external devices with which they communicate can be found in U.S. Patent Application Ser. No. 61/877,871, filed Sep. 13, 2013).

Battery management circuitry 84 for the rechargeable battery 36 in the IPG 10 is described in one example in commonly-owned U.S. Patent Application Publication 2013/0023943, which is incorporated herein by reference in its entirety, and shown in FIG. 2. Rechargeable battery 36 may comprise a Li-ion polymer battery, which when fully charged can provide a voltage (Vbat=Vmax) of about 4.2 Volts. However, other rechargeable battery chemistries could be used for battery 36 as well.

An external charger 90, typically a hand-held, battery-powered device, produces a magnetic non-data modulated charging field 98 (e.g., 80 kHz) from a coil 92. The magnetic field 98 is met in the IPG 10 by front-end charging circuitry 96, where it energizes the charging coil 44 by inducing a current in the coil. The induced current is processed by rectifier circuitry 46, including a rectifier and optionally a filtering capacitor and a voltage-magnitude-limiting Zener diode, e.g., to 5.5V), to establish a voltage V1 (e.g., ≤5.5V), which voltage is passed through a back-flow-prevention diode 48 to produce a DC voltage, Vdc. Transistors 102 coupled to the charging coil 44 can be controlled by the IPG 10 (via control signal LSK) to transmit data back to the external charger 90 during production of the magnetic field 98 via Load Shift Keying, as is well known.

Vdc is provided to battery management circuitry 84, which may reside on an Application Specific Integrated Circuit (ASIC) along with other circuitry necessary for IPG 10 operation, including current generation circuitry (used to provide specified currents to selected ones of the electrodes 16); telemetry circuitry (for modulating and demodulating data associated with telemetry coil 42 of FIG. 1B); various measurement and generator circuits; system memory; etc. The front-end charging circuitry 96 and the battery 36 typically comprise off-chip (off-ASIC) components, along with other electronics in the IPG 10, such as the telemetry coil 42; various DC-blocking capacitors coupled to the electrodes 16 (not shown); a microcontroller 100, which can communicate with the ASIC (and the battery management circuitry 84) via a digital bus 88; and other components of lesser relevance here. Microcontroller 100 may comprise in one example Part Number MSP430, manufactured by Texas Instruments, which is described in data sheets at http://www.ti.com/lsds/ti/microcontroller/16-bit_msp430/ overview.page?DCMP=MCU_other& HQS=msp430, which is incorporated herein by reference. The ASIC may be as described in U.S. Patent Application Publication 2012/0095529, which is also incorporated herein by reference.

The battery management circuitry 84 in FIG. 2 is comprised of two circuit blocks: charging circuitry 80 for generating a current for charging the battery 36, and load isolation circuitry 82 for controllably connecting or disconnecting the battery 36 from the load 75 that the battery 36 powers during normal operation of the IPG 10. Load 75 can comprise both on-chip (on-ASIC) circuit blocks such as the current generation circuitry and the telemetry circuitry mentioned earlier, and off-chip (off-ASIC) components such as the microcontroller 100.

As depicted, the charging circuitry 80, the load isolation circuitry 82, and the battery 36 generally have a T-shaped topology, with the charging circuitry 80 intervening between front-end charging circuitry 96 (Vdc) and the positive terminal (Vbat) of the battery 36, and with the load isolation circuitry 82 intervening between Vbat and the load 75.

The load isolation circuitry 82 can prohibit the battery 36 (Vbat) from being passed to power the load (Vload) dependent on a number of conditions. For example, if the load 75 is drawing a significantly high current (as indicated by overcurrent detection circuitry 74 via assertion of control signal OI), or if Vbat is too low (as indicated by undervoltage detection circuitry 70 via assertion of control signal UV), or if an external magnetic field signal μ is indicated by a Reed switch 78 (e.g., in an emergency condition warranting presentation by the patient of an external shut-off magnet), the load 75 will be decoupled from Vbat via switches 62 or 64, as assisted by OR gate 76. Discharge circuitry 68 is also provided to intentionally drain the battery 36 if Vbat is too high.

Of greater relevance to the present disclosure is the charging circuitry 80, which begins at Vdc—the DC-voltage produced by the front-end charging circuitry 96 in response to the external charger 90's magnetic field 98. Vdc splits into two paths in the charging circuitry 80 that are connected in parallel between Vdc and Vbat: a trickle charging path, and an active charging path, either of which can be used to provide a charging current (Ibat) to the battery 36 (Vbat).

The trickle charging path is passive, i.e., its operation is not controlled by control signals, and requires no power other than that provided by Vdc to produce a charging current (Itrickle) for the battery 36. As shown, the trickle charging path presents Vdc to a current-limiting resistor 50 and one or more diodes 52, and is used to provide a small charging current, Itrickle, to the battery 36. Using a small trickle charging current is particularly useful when the battery 36 is significantly depleted, i.e., if Vbat is below a threshold Vt1, such as 2.7V for example.

To produce Itrickle, Vdc must be higher than the sum of the voltage drops across the resistor 50 and diode(s) 52 and the voltage of the battery 36, Vbat. Under typical conditions and assuming three diodes 52 and a 200-ohm resistor 50 are used, the drop across the resistor 50 and diode(s) 52 will be about 2.0 Volts. Therefore, Itrickle will passively flow into the battery 36 if Vdc is greater than about 2.0V+Vbat. If this condition is not met—which would indicate that Vdc is too small (perhaps because the coupling between the external charger 90 and the IPG 10 is poor), or that Vbat is too high (which may occur as the battery 36 is gradually charged)—diodes 52 will prevent the battery 36 from draining backwards through the trickle charging path. Itrickle is generally on the order of ten milliamps. This is desirably small, because a significantly depleted rechargeable battery 36 can be damaged if it receives charging currents (Ibat) that are too high, as is well known.

The active charging path proceeds in FIG. 2 from Vdc to the battery 36 through a current/voltage source 56, which is used to produce charging current Iactive. In the example of FIG. 2, the active charging path also passes through control and protective measures of the battery management circuitry, including a charging current sense resistor 58 used in conjunction with a charging current detector 72, and an overvoltage protection switch 60 used in conjunction with an overvoltage detector 66 to open circuit the active charging path if the battery voltage, Vbat, exceeds a maximum value (such as Vmax=4.2V).

Circuitry for the current/voltage source 56 in the active charging path is shown in FIG. 3A. As its name implies, source 56 can be controlled to provide either a constant current or a constant voltage to the battery 36 during active charging. The source 56 comprises a current mirror comprised of P-channel transistors 104 and 106, which is powered by Vdc and receives a reference current, Iref, provided by reference current generator circuitry 113. Current mirror control transistor 104 mirrors a representation of Iref in current mirror output transistor(s) 106 to produce the active charging current, Iactive. In the example shown, M output transistors 106 are wired in parallel, and thus the current provided by output transistor(s) 106 equals Iactive=M*Iref. A single wider output transistor 106 (M times wider than the current mirror control transistor 104) could also be used.

The reference current generator circuitry 113 used to produce Iref is adjustable via control signals Itrim[2:0], and also comprises a current mirror. As shown, a system reference current, I' (e.g., 100 nA), is mirrored transistors 116, 118, and 120, each of which are coupled in series to gating transistors controlled by the Itrim control signals. Transistors 116, 118, and 120 are preferably of different widths, or comprise different numbers of transistors in parallel, to provide different contributions to Iref. For example, transistors 116, 118, and 120 may respectively contribute I'*N, I'*2N, and I'*4N to Iref, thus allowing Iref to vary from I'*N to I'*7N in increments of I"*N, depending on which control signals Itrim0, Itrim1, and Itrim2 are active. Additional Itrim control signals and additional current mirror output transistors (e.g., 116-120) could be used to control Iref over a wider range, and/or with smaller resolution. Adjusting Iref in this manner in turn adjusts Iactive via operation of the current mirror transistor 104 and 106 discussed above.

Control signals Itrim are issued by a source controller 86, which communicates with the microcontroller 100 by a digital bus 88, and so the microcontroller 100 can control the source controller 86 to in turn control the source 56 via Itrim and other control signals discussed further below.

The mode in which the source 56 operates to generate a charging current depends on the magnitude of the battery voltage, Vbat, which is known to the microcontroller 100. If the battery 36 is significantly depleted, i.e., Vbat<Vt1 (e.g., 2.7), the microcontroller 100 commands the source controller 86 to disable the source 56 (Ch_en='0') to turn off enable transistor 108 and prevent the production of Iactive. Thus, the battery 36 in this circumstance can only be charged via the trickle charging path, and only if magnetic field 98 and Vdc are present and sufficient.

If Vbat>Vt1, but below an upper threshold Vt2 described further below (i.e., if Vt1<Vbat<Vt2), the source 56 operates in a constant current mode. In this mode, the source 56 is enabled (Ch_en='1'), allowing Iactive to flow in accordance with a value represented by the Itrim control signals. When source 56 operates in constant current mode, Iactive is generally on the order of 50 milliamps. A P-channel transistor 114 in the active current path is fully on in constant current mode, thus allowing Iactive to flow to the battery 36 without resistance.

If Vbat>Vt2 (e.g., 4.0 V), the source 56 operates in a constant voltage mode. Ch_en and the Itrim control signals are still asserted in this mode. Crossing of the Vt2 threshold and switching of charging modes does not in this example rely on the microcontroller 100, but is instead affected via Vbat measurement circuitry 111 in the source 56. Vbat is determined in this circuitry 111 via a high-impedance resistor ladder, which produces a voltage Va indicative of Vbat. Va and a known band-gap reference voltage, Vref, are compared at amplifier 112. When Va>Vref, indicating that Vbat>Vt2, the amplifier 112 starts to turn off transistor 114, and the source 56 operates in constant voltage mode, providing an essentially constant voltage to the positive terminal of the battery 36. As the internal cell voltage of the battery 36 increases in this mode, its internal resistance causes Iactive to fall off exponentially, until Vbat reaches a maximum value, Vmax (e.g., 4.2V). At this point, the microcontroller 100 will consider charging of the battery 36 to be complete, and will once again assert Ch_en='0' to curtail further active charging. (Additionally, overvoltage switch 60 may also be opened). By contrast, when Va<Vref, indicating that Vbat<Vt2, the amplifier 112 turns on P-channel transistor 114, and the source 56 operates in constant current mode as described earlier. Voltage Va can be trimmed as necessary using control signals Vtrim to trim the resistance in the ladder, which essentially sets threshold Vt2.

FIG. 3B generally illustrates operation of the charging circuitry 80 to produce the charging current (Ibat) received by a severely depleted battery 36 (i.e., where Vbat is below an even lower threshold V(UV)=2.0V) as a function of time during a charging session, including the trickle, constant current, and constant voltage modes enabled by the charging circuitry 80 as described above. Also shown are typical values for the charging current in each of these modes, and the capacity of the battery 36 illustrated as a percentage.

The battery management circuitry 84 of FIG. 2 provides additional safeguards, such as diode(s) 54 connected between the trickle and active charging paths to prevent leakage of the battery 36 through the overvoltage switch 60, again as explained in the '943 Publication. Diode(s) 54 thus protect the battery 36 from inadvertently discharging through overvoltage switch 60, particularly at the inopportune time when Vbat is already critically low, and when it therefore might be difficult to provide a suitably high voltage to the gate of P-channel transistor 60 to turn it off.

SUMMARY

Circuitry for a medical device is disclosed, comprising: a rechargeable battery; control circuitry configured to determine a capacity of the battery; and source circuitry configured to provide a battery charging current to the battery, in which the control circuitry is configured to control the source circuitry to adjust a magnitude of the battery charging current in accordance with the determined capacity of the battery. The control circuitry can comprise a memory configured to store at least one parameter having an effect on a capacity of the rechargeable battery, wherein the at least one parameter is selected from a group consisting of one or more parameters relevant to: previous charging of the battery, previous use of the medical device to provide therapy, and the age of the battery; and an algorithm, wherein the control circuitry is configured to implement the algorithm to determine the capacity of the battery using the at least one parameter.

The at least one parameter may be stored as a function of time in the memory, or may be stored as a present value for use by the algorithm. The at least one parameter may also comprise a value computed from at least one other parameter measured during previous charging of the battery or previous use of the medical device.

Parameters relevant to previous charging of the rechargeable battery can comprise a number of previous charging session, a voltage of the battery at the start of a previous charging session, a voltage of the battery at the end of a previous charging session, a duration of a previous charging session, a charge provided to the battery during a previous charging session, a discharge depth comprising a difference between a voltage of the battery at the start and finish of a previous charging session, and a battery charging current provided to the battery during a previous charging session.

Parameters relevant to previous use of the medical device to provide therapy comprise a voltage of the rechargeable battery during a previous use, a load current drawn from the battery during a previous use, a power drawn from the battery during a previous use, a duration a use, and a charge drawn from the battery during a previous use.

The circuitry can further comprise a battery capacity database, in which the battery capacity database associates the at least one parameter with a change in the capacity of the battery, wherein the algorithm compares the at least one parameter to a change in the capacity in the battery capacity database to determine the capacity of the battery.

The algorithm may be configured to adjust the magnitude of the battery charging current via generation of one or more control signals for controlling the source circuitry.

The memory may further comprises a weight or priority of each at least one parameter, wherein the algorithm is configured to determine the capacity of the battery by using the weigh or priority or both the weight and priority of the at least one parameter.

The source circuitry may comprise a current mirror configured to produce the battery charging current in accordance with a received reference current. The control circuitry can be configured to adjust a magnitude of the battery charging current by adjusting a magnitude of the reference current using the one or more control signals.

The circuitry may further comprise front-end circuitry configured to generate a DC voltage upon receipt of a wireless charging field, wherein the source circuitry is powered by the DC voltage. The front-end circuitry may further comprises a coil configured to be energized by the wireless charging field, and rectifier circuitry configured to produce the DC voltage from the energized coil.

The algorithm may be configured to decrease the magnitude of the battery charging current if the capacity of the rechargeable battery is determined to be decreasing.

A method for recharging a rechargeable battery a medical device such as that configured as just described is also disclosed, comprising: determining a capacity of the rechargeable battery; and adjusting a magnitude of a battery charging current provided to the battery in accordance with the determined capacity of the rechargeable battery. The capacity of the battery can be determined in accordance with the at least one parameter as described above. The method may further generate a DC voltage upon receipt of a wireless charging field, wherein the DC voltage provides power for providing the battery charging current, with the DC voltage being generated by the front-end circuitry described above.

The method may decrease the magnitude of the battery charging current if the capacity of the rechargeable battery is determined to be decreasing, and the battery charging current may be generated by source circuitry along an active charging path, in which the magnitude of the battery charging current is adjusted by controlling the source circuitry. The battery charging current may also be provided to the battery along a passive trickle charging path comprising a resistance, in which the magnitude of the battery charging current is adjusted by adjusting the resistance. The method may be implemented a plurality of times over a lifetime of the medical device to adjust the magnitude of the battery charging current.

Alternative battery charging circuitry for a medical device is also disclosed, comprising: a rechargeable battery; front-end circuitry configured to generate a DC voltage upon receipt of a wireless charging field; a passive trickle charging path between the DC voltage and the battery configured to pass a first battery charging current to the battery, the trickle charging path comprising a resistance; and control circuitry configured to adjust the resistance.

The control circuitry in this alternative can be further configured to implement an algorithm, in which the algorithm is configured to determine a capacity of the rechargeable battery. The algorithm may further be configured to adjust the resistance in accordance with the determined battery capacity, with the algorithm is configured to increase the resistance if the capacity of the rechargeable battery is determined to be decreasing. The circuitry may also comprise the memory configured to store at least one parameter as described above, with the algorithm configured to determine a capacity of the rechargeable battery using the at least one parameter. The circuitry may also comprise a battery capacity database as described above, with the algorithm comparing the at least one parameter to a change in the capacity in the battery capacity database to determine the capacity of the battery. The resistance may be comprised of a plurality of resistor stages, with the control circuitry is configured to adjust the resistance by programming the resistor stages to be included or not included in the resistance. The resistor stages may be destructively programmed. The trickle charging path may further comprise at least one diode forward biased from the DC voltage to the battery. The circuitry may further comprise an active charging path between the DC voltage and the battery configured to pass a second battery charging current to the battery, with the active charging path further comprising source circuitry for generating the second battery charging current. The source circuitry may be is enabled to generate the second battery charging current when a voltage of the battery is above a threshold.

BRIEF DESCRIPTION OF THE DRAWINGS

FIGS. 1A and 1B show an implantable pulse generator (IPG) with a rechargeable battery in plan and cross sectional views, in accordance with the prior art.

FIG. 3A shows circuitry for a current/voltage source in the active current path, while

FIG. 5A shows a capacity-relevant parameter log, FIG. 5B shows present capacity-relevant parameters determined from the log, and FIG. 5C shows a battery capacity database, which are used in accordance with a charging adjustment algorithm to adjust the charging currents, in accordance with an aspect of the invention.

FIGS. 6C through 6F show various manners in which the adjustable resistance may be configured, in accordance with an aspect of the invention.

DETAILED DESCRIPTION

Figure 2:
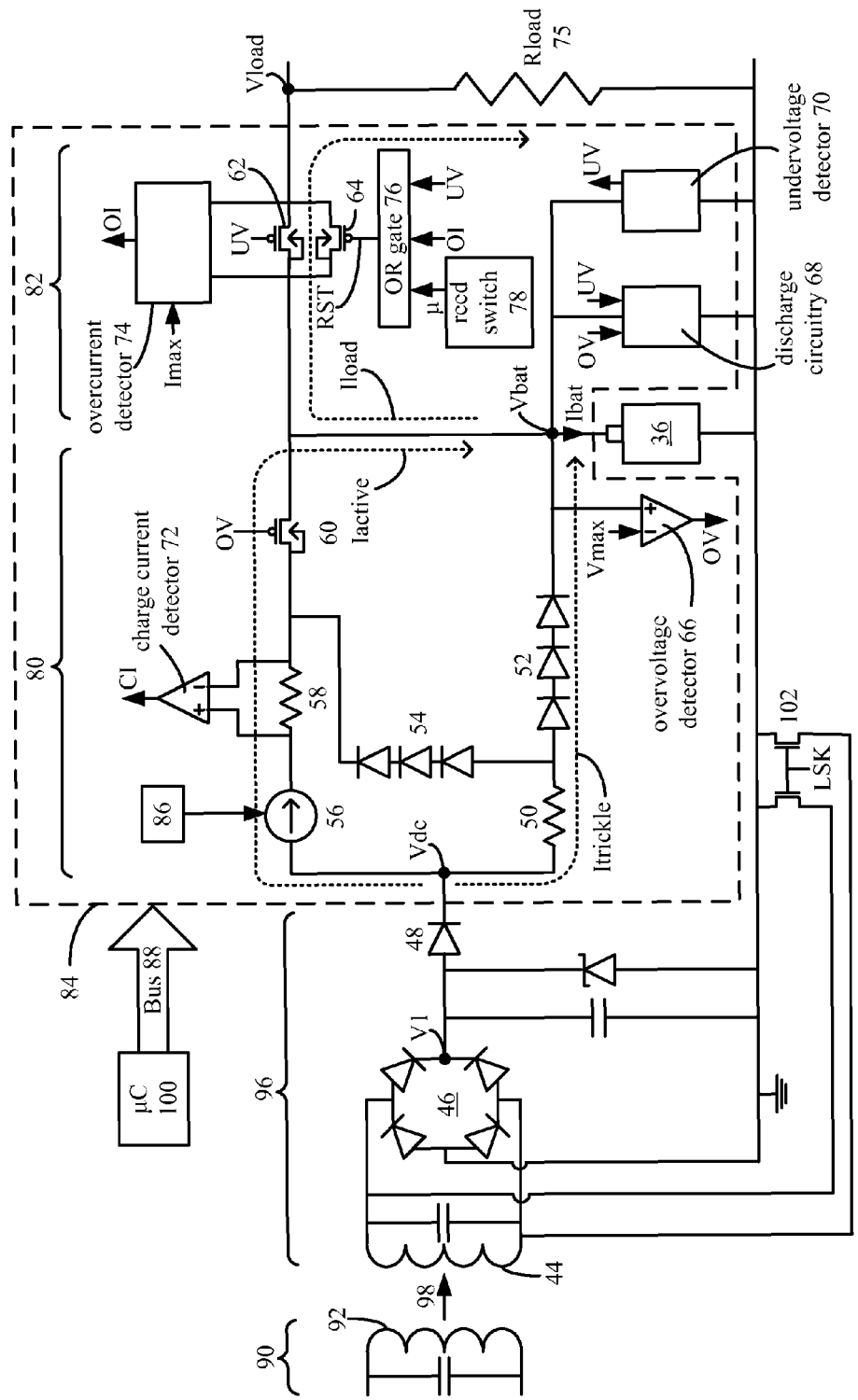
FIG. 2 shows battery management circuitry for the rechargeable battery IPG including both trickle and active charging paths, in accordance with the prior art.

The inventors are aware that certain parameters can affect the capacity of the rechargeable battery over the lifetime of an Implantable Medical Device such as an IPG, including battery calendar age (A), and various parameters pertaining to stresses imparted to the rechargeable battery. Such parameters can relate to battery charging, such as the number of times the battery has been recharged (Nc); the charging current used to recharge the battery (Ibat); how long it takes to recharge the battery (Tc), which in conjunction with the charging current determines the total charge (Cc) the battery has received (Cc=Ibat*Tc); and the discharge depth indicating the difference in the battery voltage from the start to the finish of a charging session (ΔVbat). Such parameters can also relate to use of the battery to provide power to the IMD, such as the current (Iload) or charge (Cu=Iload*Tu, where Tu equals the time of use) drawn from the battery by the load 75 during regular operational periods in which battery charging may not be occurring.

These parameters tend to reduce the capacity of the battery over time as they contribute to chemical and physical changes in the rechargeable battery. As battery capacity decreases over time, the rechargeable battery will eventually wear to a point where it can no longer be charged to operate the IPG for a significant time. Such wearing out of the battery is significant, as it requires explantation surgery to remove the IMD from the patient, either to replace the rechargeable battery in the IMD, or more likely to provide the patient with a new IMD with a fresh rechargeable battery.

Loss of battery capacity is further significant in that a rechargeable battery of reduced capacity will be more easily depleted, assuming it always draws the same power pursuant to a therapeutic stimulation program the IPG is providing to the patient. That is, Vbat will be more susceptible to dropping to unsuitably low levels, or will do so more quickly than when the battery 36 was new. If Vbat is severely depleted, i.e., if Vbat<2.0V for example, it may be difficult to recover (recharge) the battery 36. This is explained in further detail in the above-referenced 61/928,342 application, which may be used in conjunction with the disclosed technique.

The inventors have determined that it is desirable to adjust the battery charging current (Ibat) provided during a charging session to the rechargeable battery in an IMD in accordance with one or more of the capacity-relevant parameters noted above, including parameters relevant to battery charging (e.g., Nc; Ibat; Tc; Cc; ΔVbat), battery use (e.g., Iload), and/or battery age (A). Such adjustment of Ibat over time (e.g., over the life of the IMD) can occur in accordance with a battery log in the IMD which records these parameters.

Specifically, an algorithm operable in the IMD consults such parameters as stored over the history of the operation of the IMD in the battery log, and adjusts Ibat (generally, by reducing Ibat) to slow loss of battery capacity over time, which extends the life of the battery and the IPG. Such adjustment can be applied to the trickle charging current, the active charging current, or both. Although reducing Ibat may extend the time needed to charge the battery during a given charging session, such potential inconvenience to the patient should generally be inconsequential to the benefit of extending battery/IPG life, which as noted requires the significant inconvenience of IPG explanation surgery.

Figure 4:
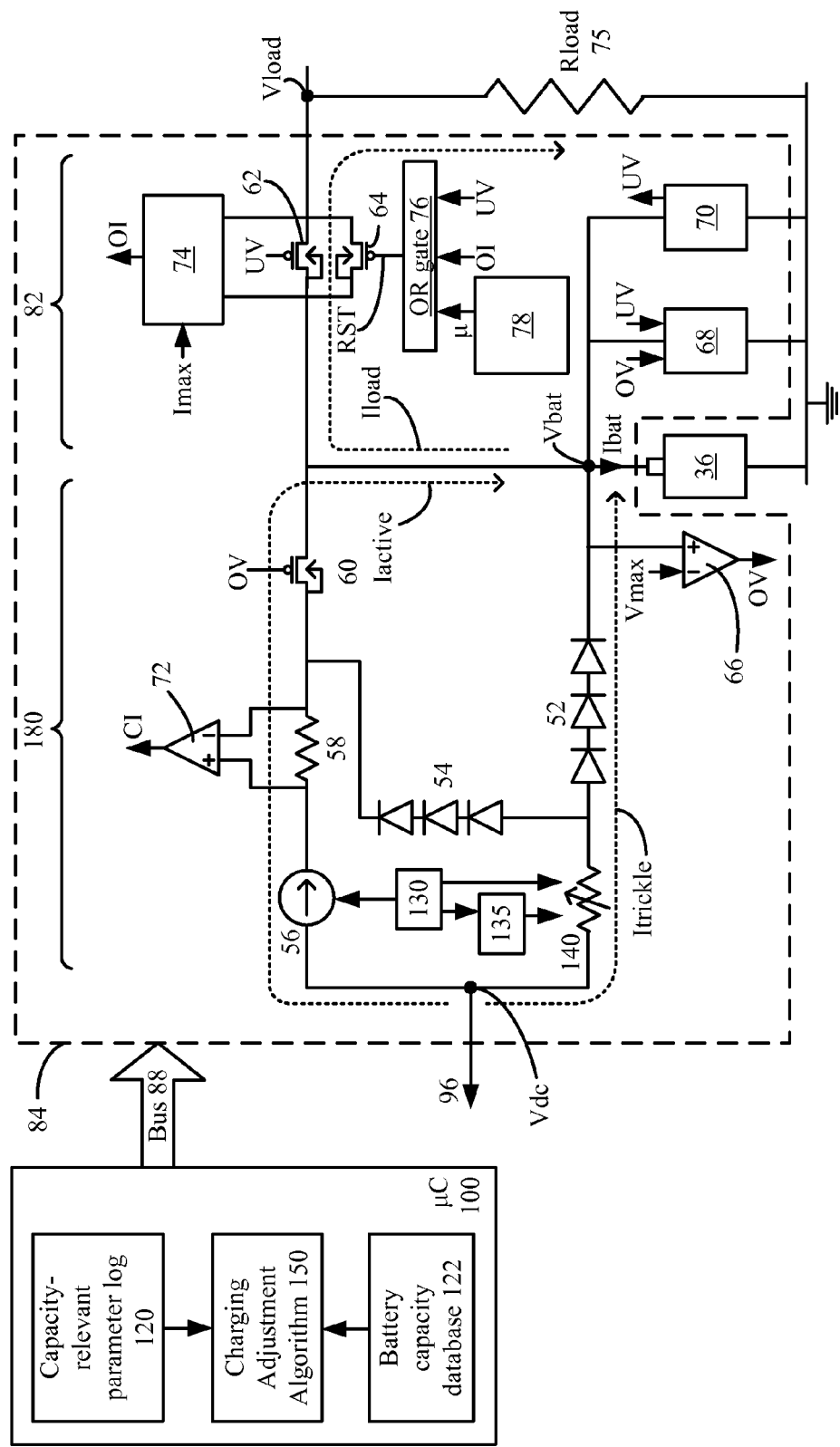
FIG. 4 shows improved battery management circuitry, and in particular improved charging circuitry which is used to adjust the trickle and active charging current in accordance with historical parameters affecting battery capacity, in accordance with an aspect of the invention.

FIG. 4 shows improved charging circuitry 180 and logic for an implantable medical device such as an IMD 10 having a rechargeable battery 36. Many of the components are unchanged from the prior art as shown in FIG. 2, and are thus not described again for simplicity.

Differences exist in the improvements of FIG. 4. First, the source controller 130 has been changed, and in addition to controlling the current/voltage source 56 also controls an adjustable resistance (Rtrickle) 140 in the trickle charging path. Such control of adjustable resistance 140 is assisted by use of a charge pump 135. These new aspects of the circuitry will be discussed with reference to FIGS. 6A-6F.

Second, the microcontroller 100 has been programmed to implement a charging adjustment algorithm 150. This algorithm 150, as will be explained in detail later, is used to control battery charging by the source 56 (via the bus 88 and source controller 130) in the active charging path, and trickle charging by adjusting the resistance 140 as necessary.

Input to the charging adjustment algorithm 150 are two data sets: a capacity-relevant parameter log 120, and a battery capacity database 122, which are shown in detail in FIGS. 5A-5C. Stated simply, the capacity-relevant parameter log 120 contains historical parameters such as those discussed above that have an impact on battery capacity, including data regarding past charging and use of the IMD 10 and its age. The battery capacity database 122 comprises data correlating the parameters to battery capacity. This database 122 is preferably programmed by the manufacturer based on its understanding of the relevance of the parameters to the particular rechargeable battery 36 at hand.

Thus, the charging adjustment algorithm 150 reviews historical parameters relevant to battery capacity in the log 120, and reviews such parameters in light of the correlations in the database 122, to adjust and control battery charging appropriately over the life of the IPG 10 in a manner to preserve battery capacity and extend its life.

Although the capacity-relevant parameter log 120 and the battery capacity database 122 are shown as programmed into the memory of the microcontroller 100, they could instead reside outside of the microcontroller 100 and made accessible to the charging adjustment algorithm 150, which would typically operate in the microcontroller 100.

One example of the capacity-relevant parameter log 120 is shown in FIG. 5A. Note that some or all of the data in the log 120 may already be stored during normal operation of the IMD 10, and thus log 120 merely shows the collection of such data in a convenient form. For ease of viewing, the capacity-relevant parameter log 120 has been split into three sections 120c, 120u, and 120a.

Section 120c contains historical parameters procured or computed during previous charging sessions, including the number of the charging session (Nc); the voltages of the battery 36 at the start and finish of the charging session (Vbat(i), Vbat(f)), from which the discharge depth (ΔVbat) can be computed; and the charging current, Ibat. Note that Ibat preferably comprises a measurement of the actual current provided by the source 56 in the active charging path, as opposed to the Iactive value to which the source 56 was programmed (by the Itrim control signals). This is preferable, because programming the source 56 (FIG. 2) to provide a particular Iactive does not guarantee that such current was actually provided to the battery 36. This is particularly true if the coupling between the external charger 90 and the IMD 10 is poor, providing a Vdc to the source 56 that is too low to produce the programmed current. The actual Ibat in the log 120 may be measured using by sensing a voltage drop across charging current sense resistor 58 using charging current detector 72, which produces an analog signal CI that can be digitized (FIG. 2).

Note that Ibat in the capacity-relevant parameter log 120 contains no data concerning the trickle charging path (Itrickle) during the relevant charging session. As Itrickle is generally low compared to Iactive, its contribution as a parameter relevant to battery capacity may be insignificant, and thus ignored. This is fortunate, because Itrickle may be difficult to accurately measure, as Vbat is low, and the IMD 10 circuitry thus unreliable, when significant trickle charging is occurring.

Also shown in section 120c is the duration of the charging session (Tc). This may be determined using the IMD's internal clock, as reflected in the timestamp values that are optionally provided in the log 120. From the charging time Tc, a total charge (Cc) provided to the battery during the charging session may be computed (Ibat*Tc).

Section 120u shows parameters relevant to battery capacity during regular use of the IMD 10, for example, to provide therapy to the patient. As noted above, the power drawn by the IMD 10 (e.g., Iload) affects battery capacity, and so Iload is included in 120u. Although not shown, the battery voltage Vbat could also be provided in 120u, which would provide a truer indication of power draw (P=I*V), which may also be included as a parameter in 120u. Use durations (Tu) are also provided, from which a total charge (Cu) can be determined (Iload*Tu). Note that Iload is a dynamic parameter when the IMD 10 operates, and will be significantly higher during those time periods when the IMD 10 is actually providing pulses to the electrodes 16. As such, the frequency, duration, and intensity of such pulses will affect (or largely determine) Iload and Cu, which may represent a scaled or average value. See, e.g., U.S. Patent Application Ser. No. 61/873,314, filed Sep. 3, 2013. Iload can also be measured directly, using the technique disclosed in U.S. Patent Application Ser. No. 61/891,730, filed Oct. 16, 2013. Although the timestamps in sections 120c and 120u suggest for simplicity that charging and use do not overlap in time (note the interleaved timestamps, tx), this is not strictly necessary, as the IMD 10 can generally continue to be used during a charging session.

Section 120a merely shows the IMD's age, as reflected by the current timestamp. Note that the some of the parameters in log 120 that originate in battery management circuitry 84 (e.g., Ibat, Iload) can be communicated to the microprocessor 100 via the bus 88 for storage in the log 120.

The particular structure of capacity-relevant parameter log 120 can vary, and need not comprise a unified single structure or file used by the charging adjustment algorithm 150. Particularly if some of the parameters are already logged in the IMD 10 for some other reason, the parameters may reside in different data structures in the IMD, which are simply queried by the algorithm 150. The algorithm 150 may additional include the ability to compute relevant parameters (e.g., charge Cc, which equals Ibat*Tc), and so the log 120 need not pre-compute such values for the algorithm 150's convenience.

Note that the illustrated parameters comprising log 120 are subject to manufacturer preferences, and perhaps even manufacturer experience with the wear out of the particular rechargeable battery 36 used in the IMD. Thus, a manufacturer may consider some of the parameters illustrated in FIG. 5A to be irrelevant (or of only minor relevance) to battery capacity, and so may not be included in the log 120. Another manufacturer may consider additional parameters not shown to be more relevant to battery charging adjustment, and so may include such additional parameters. In short, the parameters included in the capacity-relevant parameter log 120 as illustrated in FIG. 5A should be understood as only one example of the parameters useful for battery charging adjustment.

As discussed in detail later, the charging adjustment algorithm 150 will consult the parameters in the log 120 to adjust charging currents during the life of the IPG 10. FIG. 5B shows a manner in which the data in the log 120 may be summarized for easier use by the algorithm 150 in the form of present capacity-relevant parameters 120', which summarizes the parameters for use by the algorithm at the present time. For example, the total charge imparted to the battery 36 during charging over the life of the IMD, Cc(tot), is provided, which comprises a sum of the charge values Cc from section 120c of the log 120. As shown in FIG. 5B, this summed charge is currently represented by value Cc(tot)2, which would grow over time. The total charge expended during use of the IMD, Cu(tot) is similarly provided, which is currently represented by value Cu(tot)2. Also provided in present parameters 120' is the total number of times the IMD has been charged, Nc, as represented currently by Nc4, which would comprise the last value for Nc in section 120c of the log 120. Average discharge depth, ΔVbat(avg), and average charging and use currents, Ibat(avg) and Iload(avg), are also provided by averaging the individual values in section 120c.

Present capacity-relevant parameter Z in log 120' comprises a ratio of the charge expended during use (Cu(tot)) and the charge imparted to the battery during charging (Cc(tot)). This parameter is relevant, and should ideally equal one, because the charge input to the battery and output from the battery should theoretically be the same absent a problem. Of course, the accuracy of this ratio depends on how accurately the total charges can be calculated. Nonetheless, a baseline value of Z for a properly operating IMD 10 with good battery capacity can still be established even if the total charges are imperfectly measured. If the value for Z decreases over time, this suggests that an increasing amount of charge imparted to the battery during charging is not being used by the circuitry in the IMD, and hence that a battery capacity problem may exist such as leakage in the rechargeable battery 36.

Just as the parameters included in the log 120 are subject to manufacturer preferences and experiences, so too is the data included in present parameter log 120', and the manner in which such data is digested from the log 120. To cite some simple examples, the manufacturer may consider small discharge depths (ΔVbat) to be irrelevant to battery capacity and operation of the algorithm 150, and so may exclude values smaller than a threshold from the average in 120'. Or, the manufacturer may wish to include as a present parameter in 120' the percentage of the time that the discharge depth has historically been above this threshold.

Present parameters 120' may also not necessarily reflect data occurring over the entire history of the log. For example, Ibat(avg), Iload(avg), and ratio Z may be more relevant when determined from more-recent data in the log 120, and thus may be computed using only data in the log occurring over a recent time period, such as one month. Using only a recent portion of the log 120 may be particularly useful if changes to the operation of the IMD 10 are made that would impact battery capacity.

The parameters illustrated in FIG. 5B provide merely one example useful to illustrating the disclosed technique. Present capacity-relevant parameters 120' may comprise a portion of the log 120, or be separate. Also, the present capacity-relevant parameters 120' may be automatically updated pursuant to a schedule, or computed or updated once the charging current algorithm 150 runs.

An example of the battery capacity database 122 is shown in FIG. 5C. As noted earlier, the battery capacity database 122 comprises data correlating the parameters in the log 120 (or preferably the parameters as digested in log 120') to battery capacity. As shown, the database 122 depicts how particular values for the parameters affect battery capacity. For example, if the total charge provided to the battery during charging comprises a value of Cc(tot)2 (or a value between Cc(tot)2 and Cc(tot)3), database 122 reflects that battery capacity is reduced by 2%. Note that the effect of battery capacity could also be reflected in database 122 using values other than percentages, although percentages are used herein for easy illustration.

As noted, the data in database 122 is preferably determined by the IMD or battery manufacturer based on their understanding of the effect of each of the parameters on battery capacity. For example, in determining an appropriate percentage adjustment for parameter Cc(tot), the manufacturer may experimentally determine or measure the battery capacity once Cc(tot)1, Cc(tot)2, etc. have been reached, and set the percentages in the database 122 accordingly.

As shown for simplicity in FIG. 5C, the relationship between the parameter values and the percentages in FIG. 5C are reflective of the effect of just that parameter on battery capacity, absent consideration of other parameters. Alternatively, although not shown, more complicated multiparameter relationships may be reflected. For example, database 122 may reflect a percentage dependent on two or more parameters: e.g., if Cc(tot)>A, but Iload(avg)<B, then the percentage is C %; or if ΔVbat(avg)*Ibat(avg)= P(avg)>X, then the percentage is Y, etc.

Note that most of the parameters in battery capacity database 122 reflect that battery capacity decreases (hence the negative percentages) as the values for the parameters increase. However, this is not always the case, such as for ratio Z discussed above. Moreover, while all of the parameters are shown to result in a reduction of battery capacity, this might not always be the case, as some parameters (particularly if different battery chemistries are used, or given how the various parameters are mathematically processed) might result in an increased capacity over time (a positive percentage).

Battery capacity database 122 additionally may include data regarding the weight of the parameters, or a priority in which such parameters should be applied by the charging adjustment algorithm 150 when adjusting the charging current. For example, it is seen that the manufacturer considers total charge during charging (Cc(tot)) to be the parameter having the most significant impact on battery capacity. Thus, this parameter is provided a weight of '1' (suggesting it will be fully considered by the algorithm 150 without scaling), and is accorded the highest priority. By contrast, the average discharge depth (ΔVbat(avg)) is deemed to be less significant, and thus carries a weight of 0.5 and is fourth highest in priority. Again, these weights and priorities in database 122 are subject to manufacturer preferences and experience.

Figure 6A:
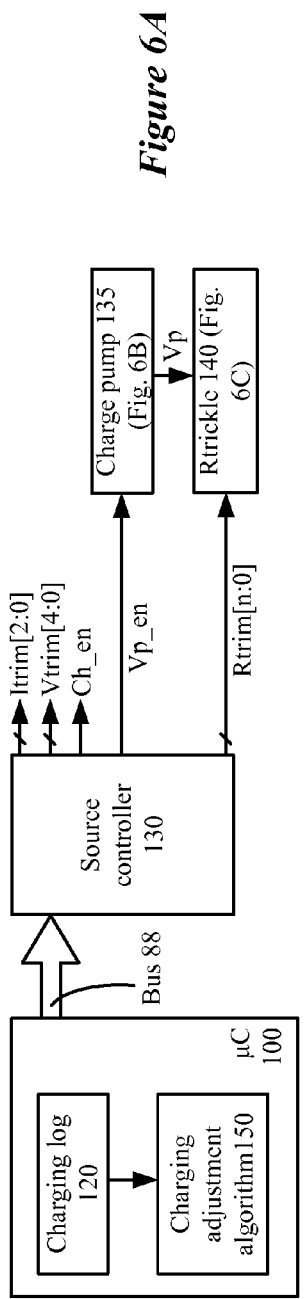
FIGS. 6A and 6B show circuitry used by the charging adjustment algorithm to adjust a resistance in the trickle charging path.

Before discussing the details of the operation of charging algorithm 150, modifications to the source controller 130 useful to the adjustment of Rtrickle 140 in the trickle charging path are shown in FIGS. 6A-6F. FIG. 6A shows the issuance of new control signals Vp_en and Rtrim[n:0] by the source controller 130, under control of the microcontroller 100 and specifically the charging adjustment algorithm 150. Control signals Rtrim[n:0] are used to adjust the resistance of Rtrickle 140. In some examples, this adjustment is permanent, and is accomplished by blowing fuses Fx (FIG. 6C-6E), or antifuses AFx (FIG. 6D, 6E) associated with Rtrickle 140. Non-destructive and reversible approaches for programming Rtrickle could also be used (FIG. 6F). Control signal Vp_en is used to enable a charge pump 135 to produce a high voltage, Vp, used to blow the fuses Fx and antifuses, and otherwise to program the resistance of Rtrickle 140.

Figure 6B:
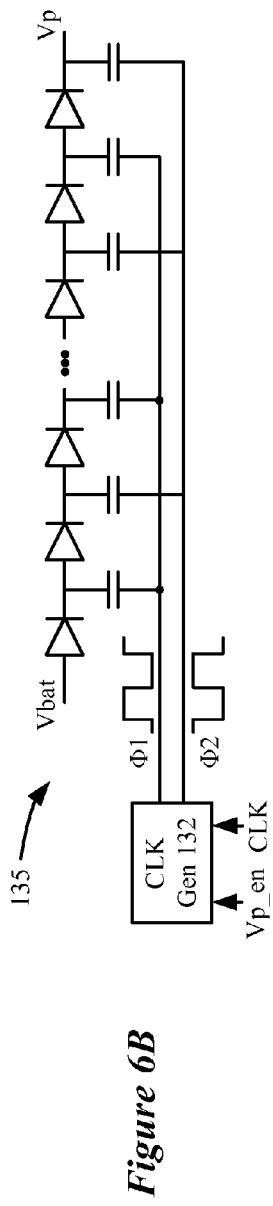

The charge pump 135 is shown in detail in FIG. 6B, and is used to produce a programming voltage Vp from a power supply in the IPG 10, which may be Vbat. Charge pump 135 is of conventional design. A clock generator 132 is used to produce clocks signals ϕ1 and ϕ2 which are out of phase and thus high at different times. The clock generator 132 can produce these clock signals from a system clock, CLK, present in the IPG 10, which clock may also be received by the microcontroller 100 and the ASIC discussed earlier. The charge pump 135 comprises a number of diode/capacitor stages, with clocks signals ϕ1 and ϕ2 boosting the voltage stored on the capacitors in odd and even stages respectively. The diodes prevent charge stored on the capacitors from leaking backward in the charge pump 135, and so the voltage at each stage increases. Using such a charge pump, the programming voltage Vp produced will be a function of the input voltage (e.g., Vbat), the magnitude of the clock signals, the number of stages used, and the threshold voltage drop across the diodes. Other high voltage generating circuits could be used instead, including different capacitor-based charge pumps, inductor-based boost converters, etc. Some of these circuits may already be present in the IPG 10 and used for other purposes, and may additionally be used from time to time to produce Vp as well.

Figure 6C:
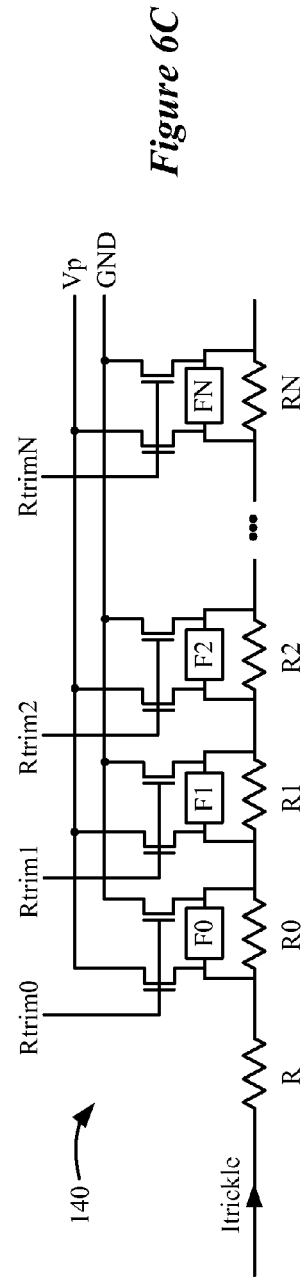

An example of an adjustable resistance Rtrickle 140 is shown in FIG. 6C. As shown, Rtrickle comprise a main resistor R, which may comprise the 200-ohm resistor discussed earlier in conjunction with the prior art. Included in series with R are a number of stages, each comprising a trimming resistor Rx and a fuse Fx which are coupled in parallel. Fuses Fx may be of conventional design as used in integrated circuitry technology, and can be formed in many different ways. Trimming resistors Rx would be smaller that main resistor R, and may comprise 10 ohms for example.

Just as Iactive is generally reduced over the life of the IPG 10 in accordance with the parameters stored in the capacity-relevant parameter log 120, so too is Itrickle generally reduced by operation of the Rtrim control signals, as these same parameters would also suggest that adjustment of Itrickle is warranted. In this regard, Rtrickle 140 in a new IPG 10 is preferably at its lowest point, and thus none of the fuses Fx are blown initially. As such, the trimming resistors Rx are bypassed through the fuses Fx, and Rtrickle=R. At various times, the charging adjustment algorithm 150 may decide that Rtrickle 140 should be adjusted (e.g., increased). When this occurs, the algorithm causes microcontroller 100 to issue signals via bus 88 to the source controller 130, which in turn will assert Vp_en and one or more of control signals Rtrim.

Assume for example that the charging adjustment algorithm 150 has decided that trimming resistor R0 is to be programmed in series with main resistor R to increase Rtrickle 140. (As discussed further below, such programming of Rtrickle 140 preferably occurs after the battery 36 has been charged. This ensures Vbat is high enough to reliably produce the voltages and control signals necessary to program Rtrickle 140). The source controller 130 would preferably issue control signal Vp_en first to provide the charge pump 135 time to produce a suitable programming voltage, Vp. Once Vp is established, the source controller 130 issues control signal Rtrim0 associated with trimming resistor R0. As shown in FIG. 6C, this control signal is presented to transistors coupled to both sides of fuse F0, which causes Vp and ground to be presented across F0 to blow it open. (Although not shown, the Rtrim control signals may be level shifted to Vp to ensure proper control of the transistors. Notice that downstream diodes 52 (FIG. 4) forward biased from Vdc to Vbat prevent Vbat from shorting to ground during programming).

Thereafter, trimming resistor R0 is no longer bypassed in the trickle charging path, and thus the resistance of Rtrickle 140 is increased to R+R0, thus decreasing Itrickle. Over time, as indicated by the charging adjustment algorithm 150, Rtrickle can be further increased to add R1 (by blowing fuse F1 in accordance with Rtrim1), etc. Rtrickle and Itrickle are thus adjustable over the life of the IPG 10. Once programmed, such adjustment is passive, and does not rely on control signals that must be asserted during trickle charging, when active control may not be reliable.

It should be noted that the means used to adjust Itrickle illustrated in FIGS. 6A-6C is merely a simple example for illustration purposes, and that many changes could be made. For example, as shown in FIG. 6D, one or more stages in Rtrickle 140 could include an antifuse (AF) programmable from an open to a shorted state. Thus, before programming, antifuse AF is opened, and trimming resistor RX is included in Rtrickle (R+RX). After programming, the antifuse bypasses RX, whose resistance is then removed from Rtrickle. Note that this provides an example of a manner in which Rtrickle 140 can be decreased over time, either as determined by algorithm 150 or for other reasons.

In another example shown in FIG. 6E, trimming resistors in one or more stages of Rtrickle 140 are connected in parallel. As shown, some of the trimming resistors are connected in series with fuses, while others are serially connected to antifuses. Thus, before programming, the trimming resistors with fuses are coupled in parallel with trimming resistor RY, and so contribute to reducing the resistance of the stage to a value lower than RY. Programming (opening) of the fuses allow the overall resistance of the stage to be increased, while programming (shorting) of the antifuses allows the overall resistance to be decreased, thus allowing Rtrickle to be increased or decreased, and Itrickle to be respectively decreased or increased.

FIG. 6F shows another example in which one or more stages of Rtrickle 140 are programmed non-destructively using non-volatile memory cells. As shown, a transistor with a floating gate appears across a trimming resistor. When control signal Rtrim is asserted, control voltages are passed to the transistor to allow it to be programmed by storing negative charge on the floating gate to turn the transistor off (depletion mode), or erased by removing negative charge on the floating gate to turn the transistor on (enhancement mode). Preferably, such control of the floating gate transistor occurs to a degree that the floating gate can passively control operation of the transistor during trickle charging without assertion of transistor control signals, and regardless of voltages such transistor control signals might float to. One skilled in the art will appreciate that the control voltages provided to the floating gate to either program or erase will differ, and may be generated by different charge pumps. In short, by programming the floating gate transistor, the trimming resistor RZ is included in Rtrickle and Itrickle is decreased. By erasing the floating gate transistor, the trimming resistor RZ is bypassed, and Itrickle is increased.

It should be noted that while concerns regarding battery capacity and extending rechargeable battery life in an IPG have motivated the disclosed adjustment to Rtrickle and Itrickle, the inventors believe such adjustments to be novel in their own right. This is significant, as one may wish to adjust Itrickle or Rtrickle for reasons not related to battery capacity considerations. In one example, it may be desirable to adjust Itrickle via Rtrickle because Vdc—the voltage produced by front-end charging circuitry 96 (FIG. 2)—may vary from patient to patient. Vdc varies in accordance with the coupling between the charging coil 92 in the external charger 90 and the charging coil 44 in the IPG 10, which coupling is affected by distance, axial offset, and angular offset between the coils. See, e.g., U.S. Patent Application Publication 2013/0096651. Because different patients will have IPGs implanted at different depths and angles, Vdc can be different between patients. A first patient with a shallow (well-coupled) IMD may register a higher Vdc, and hence a higher Itrickle, than would a second patient having a deep (poorly-coupled) IMD. Accordingly, it may be useful to use the disclosed adjustment to the trickle charging path to either decrease the first patient's baseline Itrickle current (by increasing Rtrickle), or to increase the second patient's baseline Itrickle current (by decreasing Rtrickle). Such adjustments were not possible in the prior art (e.g., FIG. 2) because the resistance of the trickle charging path (e.g., resistor 50) was preset during IPG manufacture using non-adjustable components.

Figure 7A:
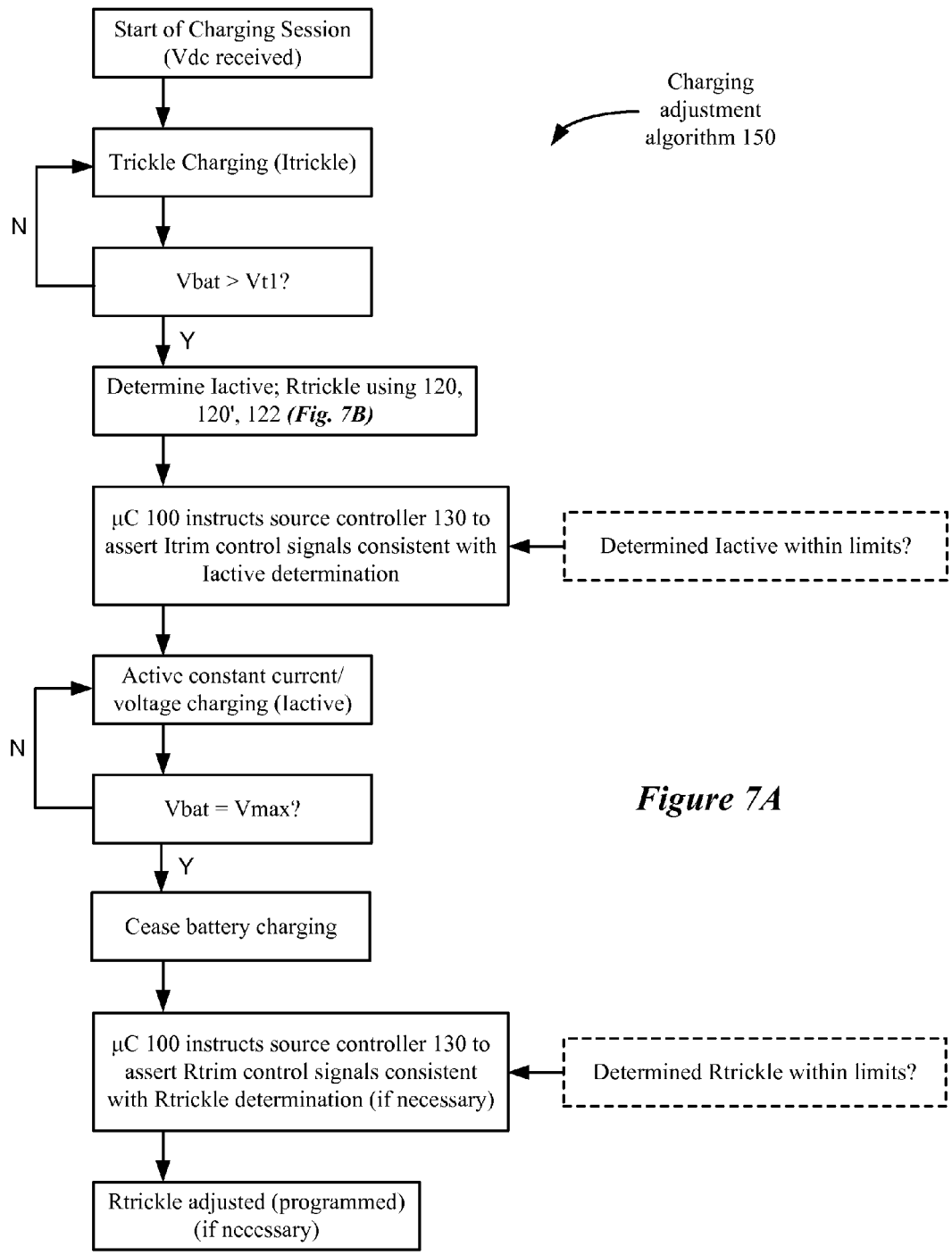
FIGS. 7A-7D show the charging adjustment algorithm illustrated in flow chart form.

FIG. 7A illustrates the charging adjustment algorithm 150 in one example. As shown, the algorithm 150 preferably begins operation whenever a charging session is begun— i.e., when the IPG 10 senses that Vdc is present suitable for charging. This is not strictly necessary however. Instead, the algorithm 150 can run on a schedule (e.g., once a month) and therefore may only determine whether adjustments are warranted on that schedule. Additionally, some portions of the algorithm 150 can run or be determined outside of a charging session.

Trickle charging can commence as discussed earlier if Vbat<Vt1=2.7V, perhaps using Rtrickle 140 as adjusted during a previous run of the algorithm 150, as will be explained later. Once Vbat>Vt1 after some amount of trickle charging, or if Vbat>Vt1 initially, algorithm 150 then prepares for active charging using source 56. In particular, the algorithm 150 at this step determines a value for Iactive (and if necessary, Rtrickle) that would be optimal given the capacity-relevant parameters log 120 (FIG. 5A), or the present capacity-relevant parameters 120' (FIG. 5B). The capacity-relevant parameters are then compared to the data in the battery capacity database 122 (FIG. 5C) to determine Iactive and/or Rtrickle. Note that determining Iactive and Rtrickle occurs at a point in the process where the battery voltage is suitably high (>2.7) to ensure such processing can occur reliably in the microcontroller 100.

Figure 7B:
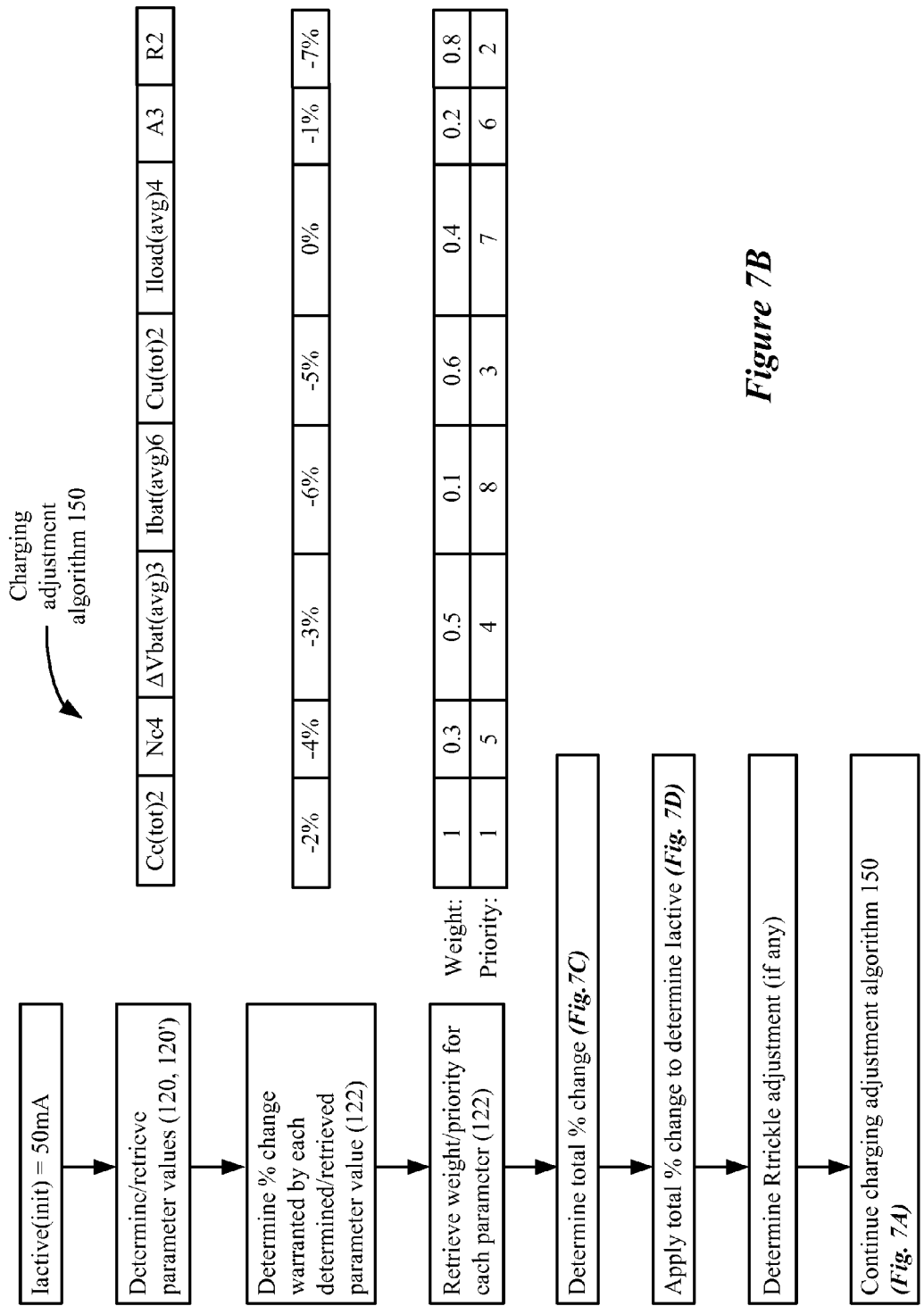

FIG. 7B illustrates further substeps that the charging adjustment algorithm 150 can implement to determine how Iactive should be adjusted. The algorithm 150 can start from the assumption of an initial value to be used for Iactive (Iactive(init)). This might be the value used for Iactive in accordance with the prior art discussed earlier (e.g., 50 mA).

The values for the present capacity-relevant parameters 120' are then queried by the algorithm 150, which the algorithm may determine from log 120 at this point if not determined and stored in advance. Then, percent changes in battery capacity warranted for each of these values are determined using battery capacity database 122, as explained earlier. Actual values for the percent changes are provided in FIG. 7B to ease understanding of subsequent processing. Additionally, the weights and priorities for each of the parameters may also be retrieved from the database 122 if present.

Figure 7C:
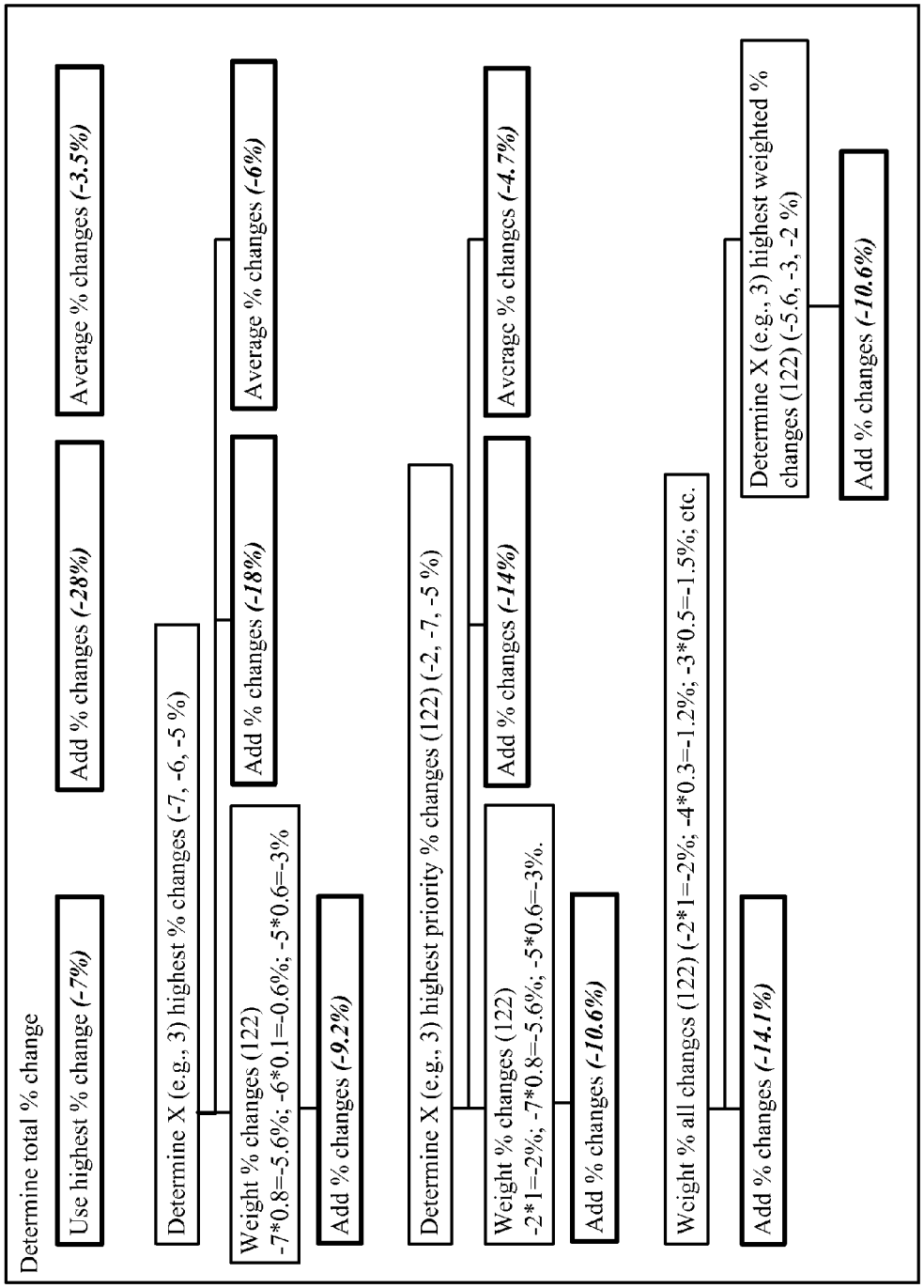

At this point, the algorithm 150 will determine a total percent change to apply to Iactive(init), and processing of the data to determine this total can occur in several different ways, some of which are shown in FIG. 7C. For example, the algorithm 150 may just use the largest percentage change (−7%) on the basis that this capacity-relevant parameter is having the largest effect on battery capacity. Alternatively, the algorithm 150 may add (−28%) or average (−3.5%) the determined percentages, so that the effect of each parameter is considered to some extent.

Alternatively, the algorithm 150 may consider only a certain number (e.g., X=3) of the highest determined percentages (−7, −6, −5%), and discard all other lower percentages from subsequent analysis as being too minimal in their effect on battery capacity. These remaining percentages can then be added (−18%) or averaged (−6%) as before. Alternatively, these remaining percentages can be weighted using the retrieved weights (if present), and added (−9.2%).

Alternatively, the algorithm 150 may consider only a certain number (e.g., X=3) of the determined percentages (−2, −7, −5%) having the highest priorities (1, 2, and 3), if such data is present. These percentages may then be added (−14%), averaged (−4.7%), or weighted and added (−10.6%) as described in the preceding paragraph.

In yet another example, the algorithm 150 may weight all of the determined percentages, if such weight data is present. These resulting weighted percentages may be then be added (−14.1%). This may comprise a most preferred manner of processing the percentages, as all are considered, with capacity-relevant parameters of lesser relevance having a smaller effect on the total percent change. Alternatively, only the most relevant of the weighted percentages may be further considered (−5.6, −3, −2%) and added (−10.6%).

All of these alternatives for processing the determined percentages to arrive at a total percentage change indicative of the overall change in battery capacity have some reasonable basis, and any of them when applied to adjust Iactive will assist in slowing the loss of battery capacity over the life of the IPG 10, albeit to different degrees. Still other ways of processing the capacity-relevant parameters are possible, depending on manufacturer preferences and experience.

Figure 7D:
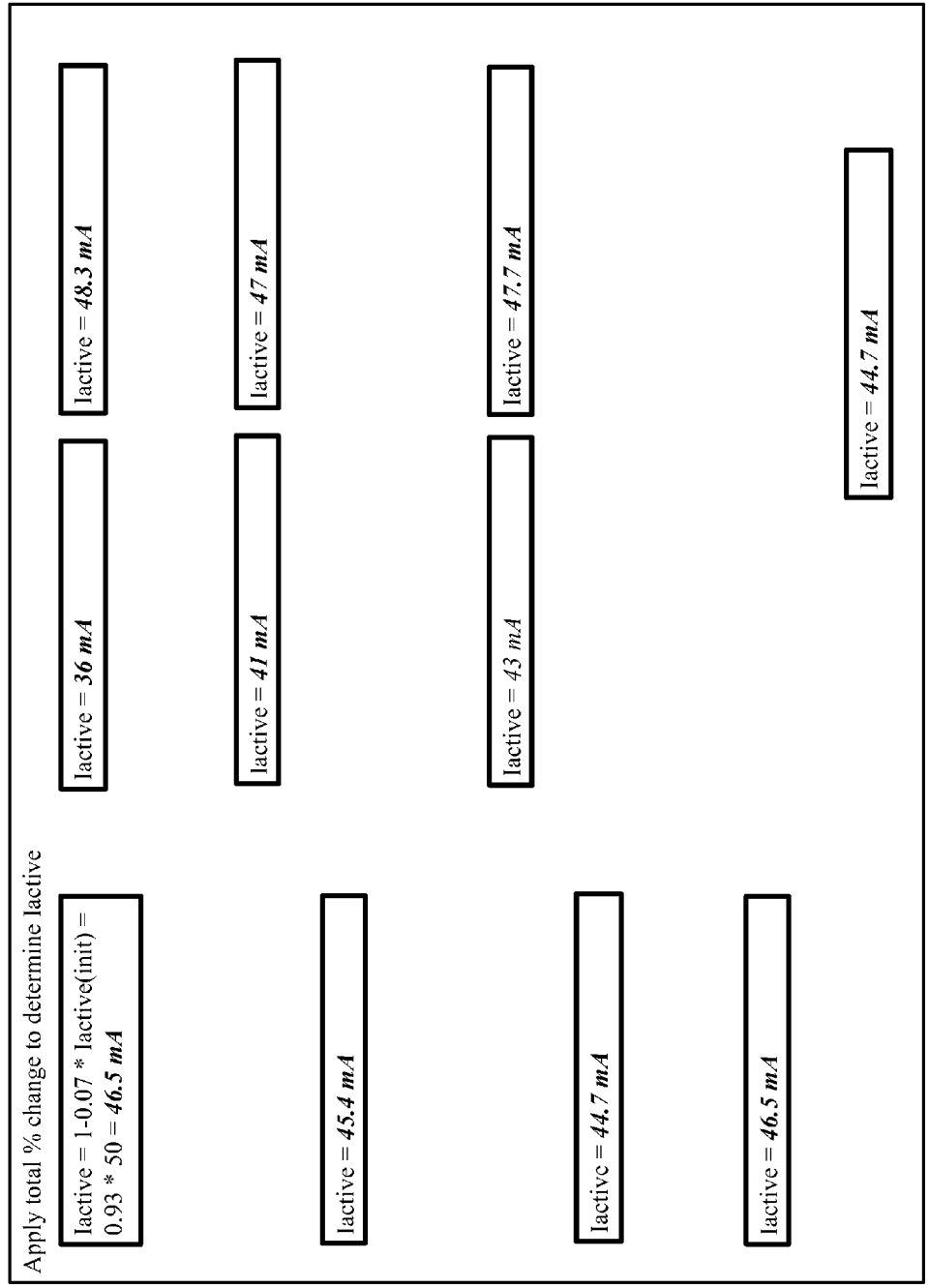

Once the total percentage change is determined, it is applied to Iactive(init) to determine the value for Iactive that should be produced by the source 56 at this point in the IPG's life to slow the decrease in battery capacity. This is shown in FIG. 7D for the various total percentages changes depicted in FIG. 7C. Although Iactive is shown as adjusted in FIG. 7D consistently with the total percentage change determined for the rechargeable battery (i.e., by the same percentage), it should be noted that such one-to-one correspondence of these percentages is not strictly required, and that other scaling or processing of the total percentage change could be performed before it is applied to Iactive (init).

Returning to FIG. 7B, the charging adjustment algorithm 150 can at this point determine whether Rtrickle should also be adjusted. Such adjustment can occur using the same total percentage change used to adjust Iactive to essentially attempt to adjust Itrickle to scale with Iactive. For example, assume that the total resistance of the trickle charging path (including Rtrickle 140 and diodes 52 (FIG. 4)) is approximately 400 ohms. Assume further for simplicity that Rtrickle 140 is formed as shown in FIG. 6C, allowing Rtrickle to be increased. Assume further that the trimming resistor in each stage can add 10 ohms to the total trickle charge path resistance, i.e., an increase of 2.5%. As the total percentage change crosses these increments (i.e., −2.5%, −5%, −7.5%, etc.), the algorithm 150 can determine that it is time to blow a next fuse in a next open stage (e.g., F0, F1, F2, etc.). In this manner, Itrickle will roughly scale with Iactive. Note that it may not be necessary for the algorithm 150 to adjust Rtrickle upon each charging session, and in fact it would be expected that programming of Rtrickle would occur only a handful of times during the life of the IPG 10, although of course this depends on the amount that each stage in Rtrickle 140 can adjust the resistance and the number of stages used.

It may not always be possible for the algorithm 150 to adjust Rtrickle in accordance with the total percentage change used by Iactive, because the configuration used for Rtrickle 140 may simply not be able to implement the change. For example, suppose the total percentage change was determined to be −3% in a previous charging session, and fuse F0 was blown at that time to increase Rtrickle 140 by 2.5%. If a later single percentage is determined to be −1%, it would be preferable to decrease Rtrickle. However, if Rtrickle is configured as shown in FIG. 6C, the resistance could not be decreased (only increased), and so the algorithm 150 would leave the resistance of Rtrickle unchanged. (Note that the Rtrickle configurations of FIGS. 6D-6F would allow Rtrickle to be decreased).

Figure 3A:
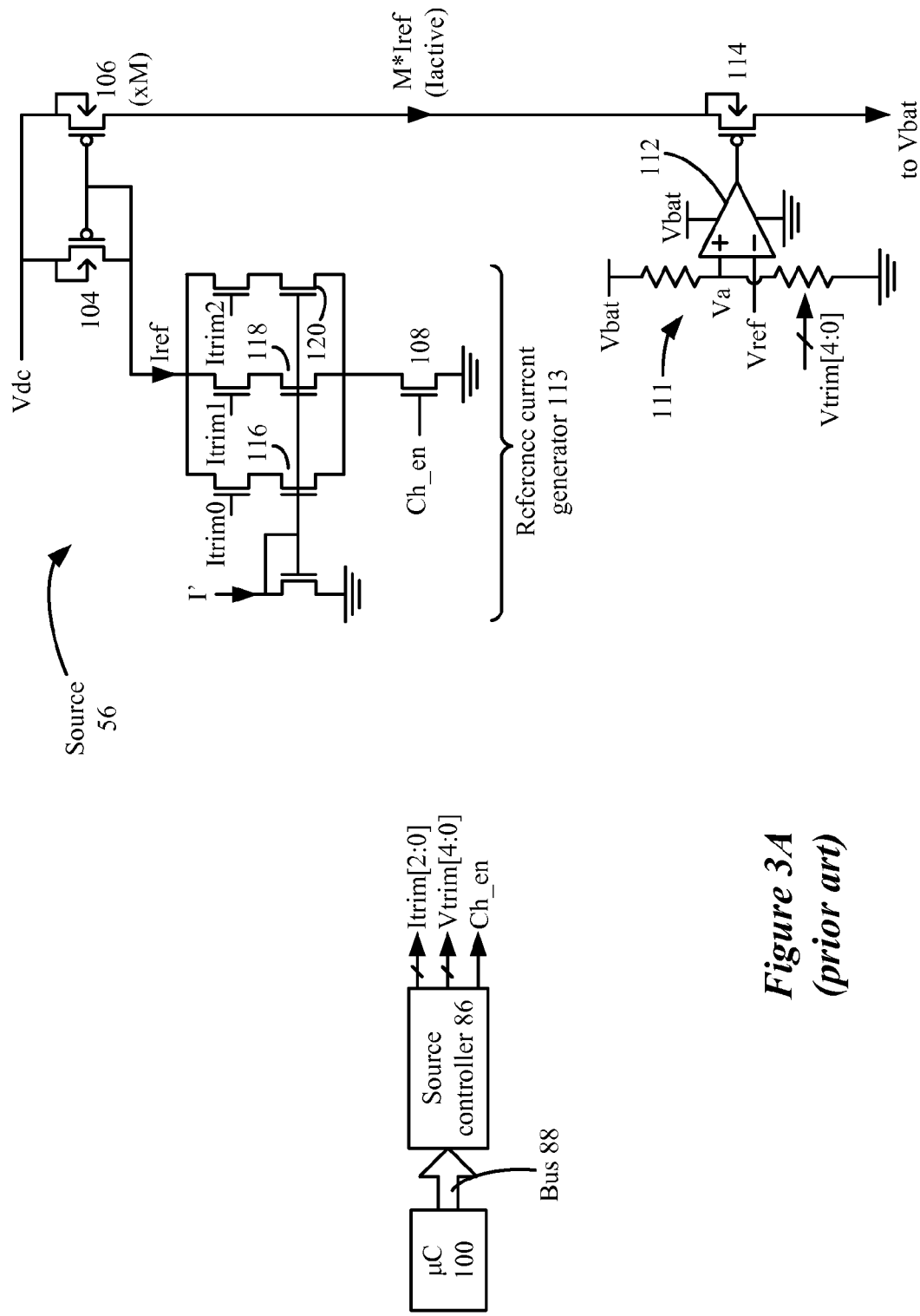
Figure 3B:
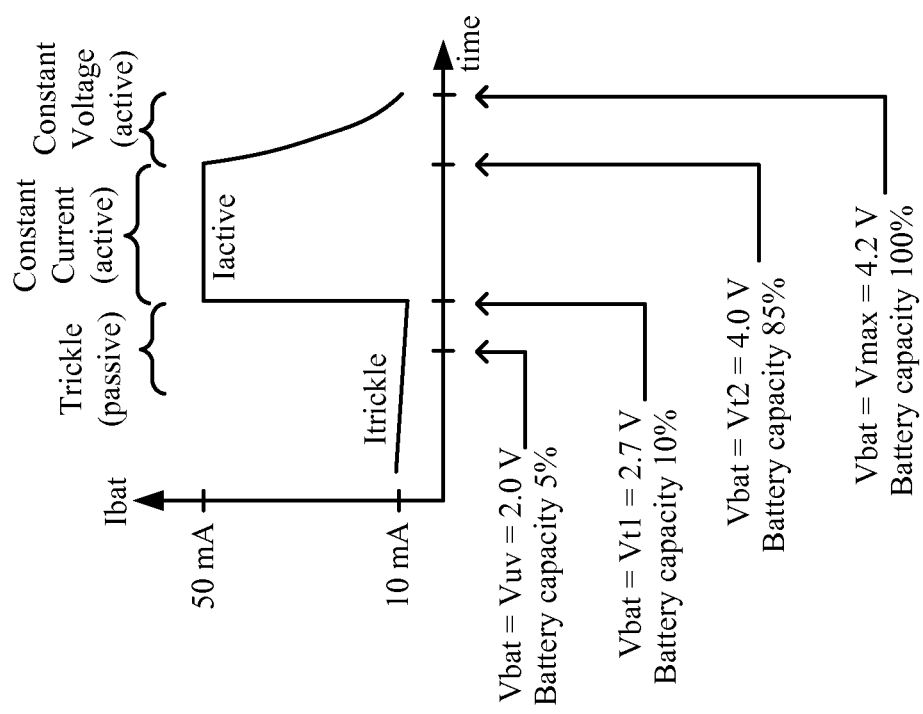
FIG. 3B shows a graph of the battery charging current provided by both the trickle and active charging paths as a function of time, in accordance with the prior art.

After Iactive and Rtrickle are determined, and returning to FIG. 7A, charging adjustment algorithm 150 next controls the source 56 to produce a charging current with the determined (adjusted) value for Iactive. As described earlier, this involves the microcontroller 100 instructing the source controller 130 via bus 88 to assert appropriate Itrim control signals. It should be noted that Iactive may be adjusted in the source 56 with a finer resolution by using a larger number of Itrim control signals (and accordingly, a larger number of stages in the reference current generator circuitry 113 (FIG. 3A)).

As shown in the dotted lined box in FIG. 7A, the charging adjustment algorithm 150 may also consider whether the determined Iactive is within limits, and may choose not to adjust Iactive beyond such limits, even if the total percentage change suggests to do this. For example, the algorithm 150 may not permit an adjustment of Iactive above or below maximum limits. For example, algorithm 150 may not permit Iactive>100 mA to be established because the source 56 may be unable to provide such a charging current, or because such a charging current could damage the IPG or be unsafe. Alternatively, algorithm 150 may not permit Iactive<8 mA for example, because charging at levels lower than this may be so insignificant (and result in such long charging session times) that benefits to slowing the reduction of battery capacity provided by the algorithm 150 are outweighed by these practical considerations.

Continuing with FIG. 7A, the battery 36 is actively charged by the source 56 at the determined Iactive, and as Vbat increases, eventually constant voltage charging will be provided as explained earlier. When the battery is fully charged (Vbat=Vmax=4.2V), charging ceases.

At this point, the charging adjustment algorithm 150 adjusts Rtrickle if necessary in accordance with its earlier determined value, even though trickle charging already occurred earlier during operation of the algorithm. In other words, Rtrickle (and hence Itrickle) is adjusted for the benefit of the next charging session. It is preferred to adjust Rtrickle at this point in the algorithm 150 because the battery 36 is now fully charged, and thus operation of the circuitry involved in programming Rtrickle 140 (FIG. 6A-6F), including the charge pump 135, should function optimally and reliably. Thus, the microcontroller 100 instructs the source controller 130 via bus 88 to assert appropriate Rtrim control signals to program Rtrickle as described earlier, and if possible. Again, the algorithm 150 may choose not to adjust Rtrickle if it would be outside of minimum or maximum limits.

It should be noted that the illustrated order of the steps performed in charging adjustment algorithm 150 is merely one example, and changes could be made to the disclosed order in manners not affecting its overall results. Additionally, not all steps are strictly necessary, and other steps could be included as well.

Figure 8:
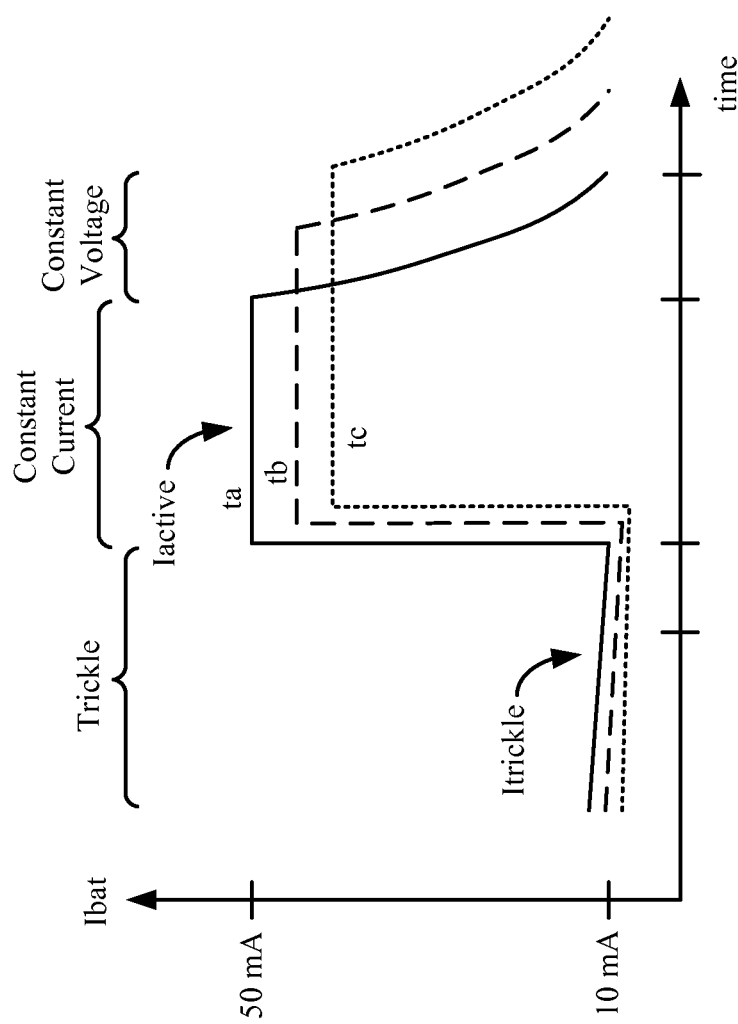
FIG. 8 shows graphs of the battery charging current provided by both the trickle and active charging paths as a function of time during different charging sessions occurring at different times over the life of the IPG, and the manner in which the charging adjustment algorithm has adjusted these currents, in accordance with an aspect of the invention.

FIG. 8 generally illustrates operation of the improved charging circuitry 180 as controlled by charging adjustment algorithm 150 to produce the charging current (Ibat) received by a severely depleted battery 36 as a function of time during charging sessions occurring at times ta, tb, and tc over the life of the IPG 10. In this example, for simplicity, it is assumed as is most often the case that the capacity-relevant parameters will generally warrant decreasing the charging current over the life of the IPG 10 to preserve battery capacity and hence extend IPG life. Thus, it is seen that both Itrickle (produced by the trickle charging path through Rtrickle) and Iactive (produced by the source 56), have decreased over time through operation of the algorithm 150. Accordingly, note as depicted that this may lengthen the time necessary to fully charge the battery 36 as well as when the charging modes change (between trickle charging, constant current, constant voltage charging), because Vbat will increase more slowly as the charging currents Itrickle and Iactive are decreased. However, note that such extension of charging time may be mitigated by the decrease in battery capacity experienced over time, which is still present although slowed in its rate though use of the disclosed technique.

While the charging adjustment algorithm 150 is disclosed as being useful to adjusting both Iactive and Itrickle, it should be noted that the algorithm can be used to adjust only one of the charging currents. Indeed, inclusion of a trickle charging path is not strictly required, as discussed in the above-referenced U.S. provisional patent application 61/928,342.

While control of the charging circuitry 180 has been disclosed as occurring in steps from the microcontroller 100 to the source controller 130, such means of dividing control is not strictly necessary. Instead, control circuitry for the charging circuitry 180, including circuitry capable of executing algorithm 150, could instead be integrated in other IMD designs, such as on a single integrated circuit. The charging circuitry 180 itself may also be integrated with such integrated control, such as the ASIC described earlier.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. Circuitry for a medical device, comprising:
a rechargeable battery;
control circuitry configured to determine a present capacity of the battery;
source circuitry configured to provide a single constant battery charging current to the battery during the entirety of a charging session; and
front-end circuitry configured to generate a DC voltage upon receipt of a wireless charging field, wherein the source circuitry is powered by the DC voltage,
wherein the control circuitry is further configured to determine a magnitude of the single constant battery charging current in accordance with the determined present capacity of the battery and to control the source circuitry to produce the determined magnitude of the single constant battery charging current during the charging session.

2. The circuitry of claim 1, wherein the control circuitry comprises memory configured to store at least one parameter having an effect on the capacity of the rechargeable battery, wherein the at least one parameter comprises one or more of: at least one first parameter determined during previous charging of the battery, at least one second parameter determined during previous use of the medical device to provide therapy, and an age of the battery;
wherein the control circuitry is configured to implement an algorithm to determine the present capacity of the battery using the at least one parameter.

3. The circuitry of claim 2, wherein the at least one parameter is stored as a function of time in the memory.

4. The circuitry of claim 2, wherein the at least one parameter is stored as a present value for use by the algorithm.

5. The circuitry of claim 2, wherein the at least one parameter comprises a value computed from at least one other parameter determined during previous charging of the battery or previous use of the medical device.

6. The circuitry of claim 2, wherein the at least one first parameter determined during previous charging of the rechargeable battery comprises one or more of a number of previous charging session, a voltage of the battery at the start of a previous charging session, a voltage of the battery at the end of a previous charging session, a duration of a previous charging session, a charge provided to the battery during a previous charging session, a discharge depth comprising a difference between a voltage of the battery at the start and finish of a previous charging session, and a battery charging current provided to the battery during a previous charging session.

7. The circuitry of claim 2, wherein the at least one second parameter determined during previous use of the medical device to provide therapy comprises one or more of a voltage of the rechargeable battery during a previous use, a load current drawn from the battery during a previous use, a power drawn from the battery during a previous use, a duration a use, and a charge drawn from the battery during a previous use.

8. The circuitry of claim 2, further comprising a battery capacity database, wherein the battery capacity database associates the at least one parameter with a change in the capacity of the battery, wherein the algorithm compares the at least one parameter to a change in the capacity in the battery capacity database to determine the present capacity of the battery.

9. The circuitry of claim 2, wherein the algorithm is configured to set the magnitude of the single constant battery charging current via generation of one or more control signals for controlling the source circuitry.

10. The circuitry of claim 2, wherein the memory further comprises a weight or priority of each at least one parameter, wherein the algorithm is configured to determine the present capacity of the battery by using the weight or priority or both the weight and priority of the at least one parameter.

11. The circuitry of claim 1, wherein the source circuitry comprises a current mirror configured to produce the single constant battery charging current in accordance with a received reference current.

12. The circuitry of claim 11, wherein the control circuitry is configured to produce the determined magnitude of the single constant battery charging current by setting a magnitude of the reference current using one or more control signals.

13. The circuitry of claim 1, wherein the front-end circuitry further comprises a coil configured to be energized by the wireless charging field, and rectifier circuitry configured to produce the DC voltage from the energized coil.

14. The circuitry of claim 2, wherein the algorithm is configured to decrease the determined magnitude of the single constant battery charging current if the determined present capacity of the rechargeable battery indicates that the battery capacity is decreasing during the life of the medical device.

* * * * *